(12) United States Patent
Sugizaki

(10) Patent No.: US 12,181,469 B2
(45) Date of Patent: Dec. 31, 2024

(54) CHEMICAL SENSOR, METHOD FOR DETECTING TARGET SUBSTANCE, AND APPARATUS FOR DETECTING THE SAME

(71) Applicant: KABUSHIKI KAISHA TOSHIBA, Tokyo (JP)

(72) Inventor: Yoshiaki Sugizaki, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 519 days.

(21) Appl. No.: 17/470,880

(22) Filed: Sep. 9, 2021

(65) Prior Publication Data
US 2022/0299505 A1    Sep. 22, 2022

(30) Foreign Application Priority Data
Mar. 18, 2021 (JP) .................. 2021-044802

(51) Int. Cl.
*G01N 33/543* (2006.01)
*G01N 33/566* (2006.01)

(52) U.S. Cl.
CPC . *G01N 33/54373* (2013.01); *G01N 33/54306* (2013.01); *G01N 33/566* (2013.01)

(58) Field of Classification Search
CPC ....... G01N 33/54373; G01N 33/54306; G01N 33/566
See application file for complete search history.

(56) References Cited

U.S. PATENT DOCUMENTS

| | | |
|---|---|---|
| 2002/0023493 A1 | 2/2002 | Miyake et al. |
| 2009/0159458 A1 | 6/2009 | Tamiya et al. |
| 2020/0080977 A1 | 3/2020 | Isobayashi et al. |

FOREIGN PATENT DOCUMENTS

| | | |
|---|---|---|
| JP | H11-505410 A | 5/1999 |
| JP | 2002-71540 A | 3/2002 |
| JP | 2009-133800 A | 6/2009 |
| JP | 2020-41947 A | 3/2020 |
| WO | WO 96/38575 A1 | 12/1996 |
| WO | WO 2007/116811 A1 | 10/2007 |

OTHER PUBLICATIONS

Ueda et al., "Open sandwich ELISA: A novel immunoassay based on the interchain interaction of antibody variable region," Nature Publishing Group, vol. 14, pp. 1714-1718 (1996).

*Primary Examiner* — Elizabeth C. Kemmerer
*Assistant Examiner* — Mckenzie A Dunn
(74) *Attorney, Agent, or Firm* — Finnegan, Henderson, Farabow, Garrett & Dunner, LLP

(57) ABSTRACT

According to one embodiment, a chemical sensor for detecting a target substance in a specimen, the chemical sensor including a sensitive film, a first extracellular region peptide of a transmembrane receptor immobilized on the sensitive film, a liquid phase disposed on the sensitive film, and a second extracellular region peptide of the transmembrane receptor contained within the liquid phase.

6 Claims, 20 Drawing Sheets

Specification includes a Sequence Listing.

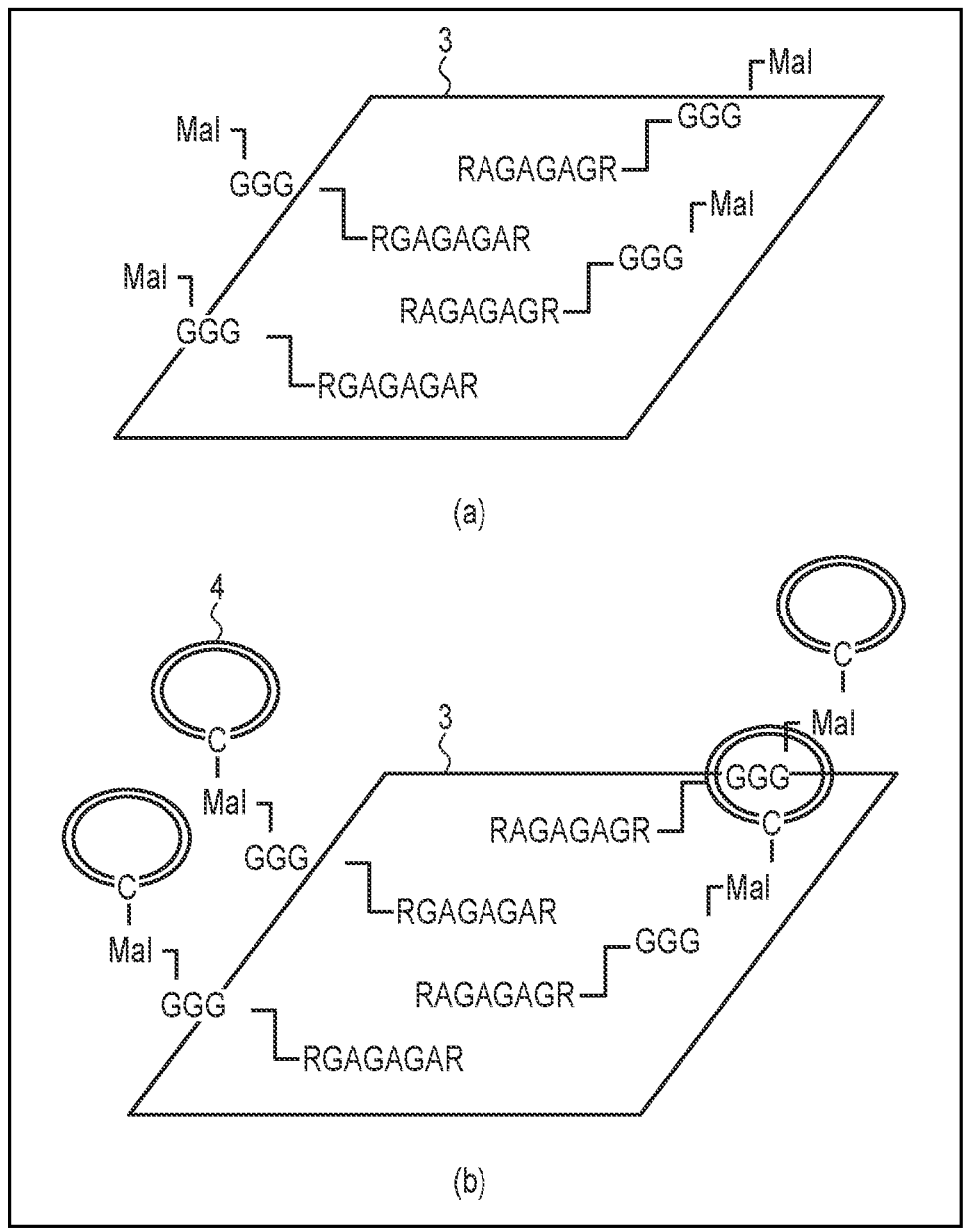
F I G. 5
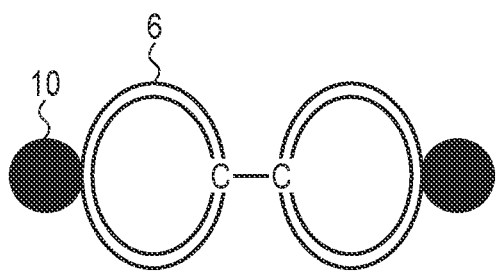
F I G. 6

CquiOR10

ECL-1: YRAWGNIDE / GCG (Sequence Number 3)

ECL-2: YPLFTGTRSLPYGMFIPGVNNFKTPLYQVFF / KCK (Sequence Number 4)

ECL-3: FLLNIIENPAQ / GCG (Sequence Number 5)

C-terminal:
(a) RGAGAGARGGG-YSYFTLLRRVYN (Sequence Number 6)
(b) CGGG-YSYFTLLRRVYN (Sequence Number 7)

ECL-1
- (a) LLQSNSLETFCES (Sequence Number 8)
- (b) LLQSNSLETFMES-KCK (Sequence Number 9)
- (c) LLQSNSLETFSES-KCK (Sequence Number 10)

ECL-2
- (a) ISASSEPTLMYPTWIPWNWRDSTSA (Sequence Number 11)
- (b) ISASSEPTLMYPTWIPWNWRDSTSA-KCK (Sequence Number 12)

ECL-3
- (a) YFLLFGNVGIMR (Sequence Number 13)
- (b) YFLLFGNVGIMR-KCK (Sequence Number 14)

C-terminal  CGGGPIS MKTFTVMIKG AYTMKTLLNEIRKTGLE (Sequence Number 15)

CqOr118

ECL-1  RAAGNFTNFLELT-KCK (Sequence Number 16)

ECL-2  YLMSGVLVRELPYFMWYWYDWHREGLYEITFF-KC (Sequence Number 17)

ECL-3  TSQISAFDLFKFVLFL-KCK (Sequence Number 18)

C-terminal
- (a) Mal-GGG-LLKTIYDPSEK (Sequence Number 19)
- (b) Mal-RGAGAGARGGG-LLKTIYDPSEK (Sequence Number 20)

F I G. 8

Odr10

ECL-1 (a) GLLKTRGKNLGTYKYLM / GCG (Sequence Number 21)

(b) GLLKTRGKNLGTYKYLM / GC (Sequence Number 22)

ECL-2 (a) VHFVYRYFATCKPNLLRLFNLPTLLLW / KK (Sequence Number 23)

(b) VHFVYRYFATMKPNLLRLFNLPTLLLW / KCK (Sequence Number 24)

(c) VHFVYRYFATSKPNLLRLFNLPTLLLW / KCK (Sequence Number 25)

ECL-3 (a) MFYCGYATWKTMNEHKDVSDRTRALQKQLFKALVLQTLI / KCK (Sequence Number 26)

(b) GYATWKTMNEHKDVSDRTRALQKQLFKALVLQ / KCK (Sequence Number 27)

C-terminal (a) LIIRDFRRTIFNFLCGKKNSVDESRSTTRANLSQVPT (Sequence Number 28)

(b) CLIIRDFRRTIFNFLMGKKNSVDESRSTTRANLSQVPT (Sequence Number 29)

(c) CLIIRDFRRTIFNFLSGKKNSVDESRSTTRANLSQVPT (Sequence Number 30)

(d) CGKKNSVDESRSTTRANLSQVPT (Sequence Number 31)

(e) Mal-GKKNSVDESRSTTRANLSQVPT (Sequence Number 32)

(f) LIIRDFRRTIFNFL / GCG (Sequence Number 33)

F I G. 9

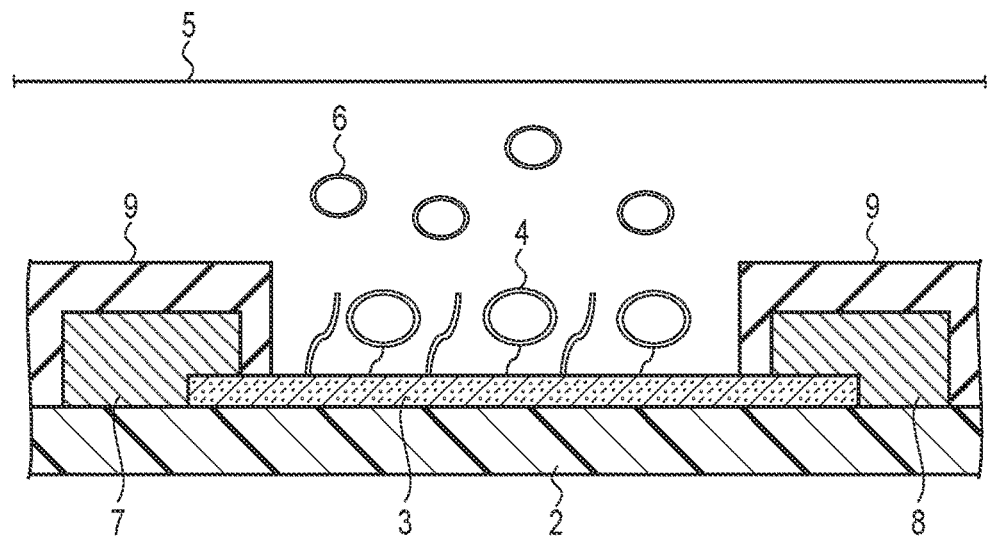
FIG. 11A
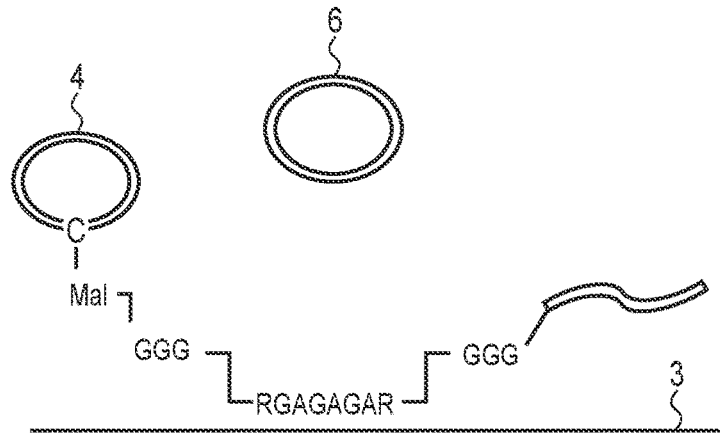
FIG. 11B
| First ECR peptide (immobilized to sensitive film) | Second ECR peptide (within liquid phase) |
|---|---|
| ECL-1 + C-terminal | ECL-2 |
| ECL-1 + C-terminal | ECL-3 |
| ECL-2 + C-terminal | ECL-1 |
| ECL-2 + C-terminal | ECL-3 |
| ECL-3 + C-terminal | ECL-1 |
| ECL-3 + C-terminal | ECL-2 |
FIG. 11C

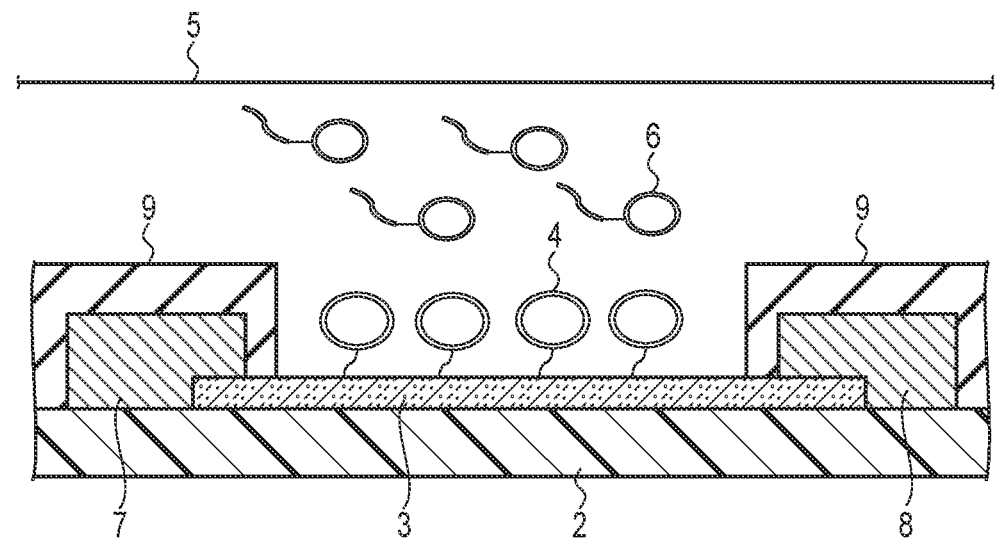
F I G. 12A
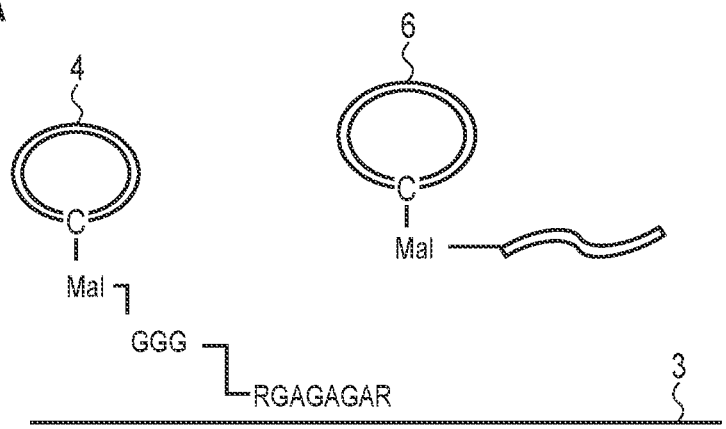
F I G. 12B
| First ECR peptide (immobilized to sensitive film) | Second ECR peptide (within liquid phase) |
|---|---|
| ECL-1 | ECL-2 + C-terminal |
| ECL-1 | ECL-3 + C-terminal |
| ECL-2 | ECL-1 + C-terminal |
| ECL-2 | ECL-3 + C-terminal |
| ECL-3 | ECL-1 + C-terminal |
| ECL-3 | ECL-2 + C-terminal |
F I G. 12C

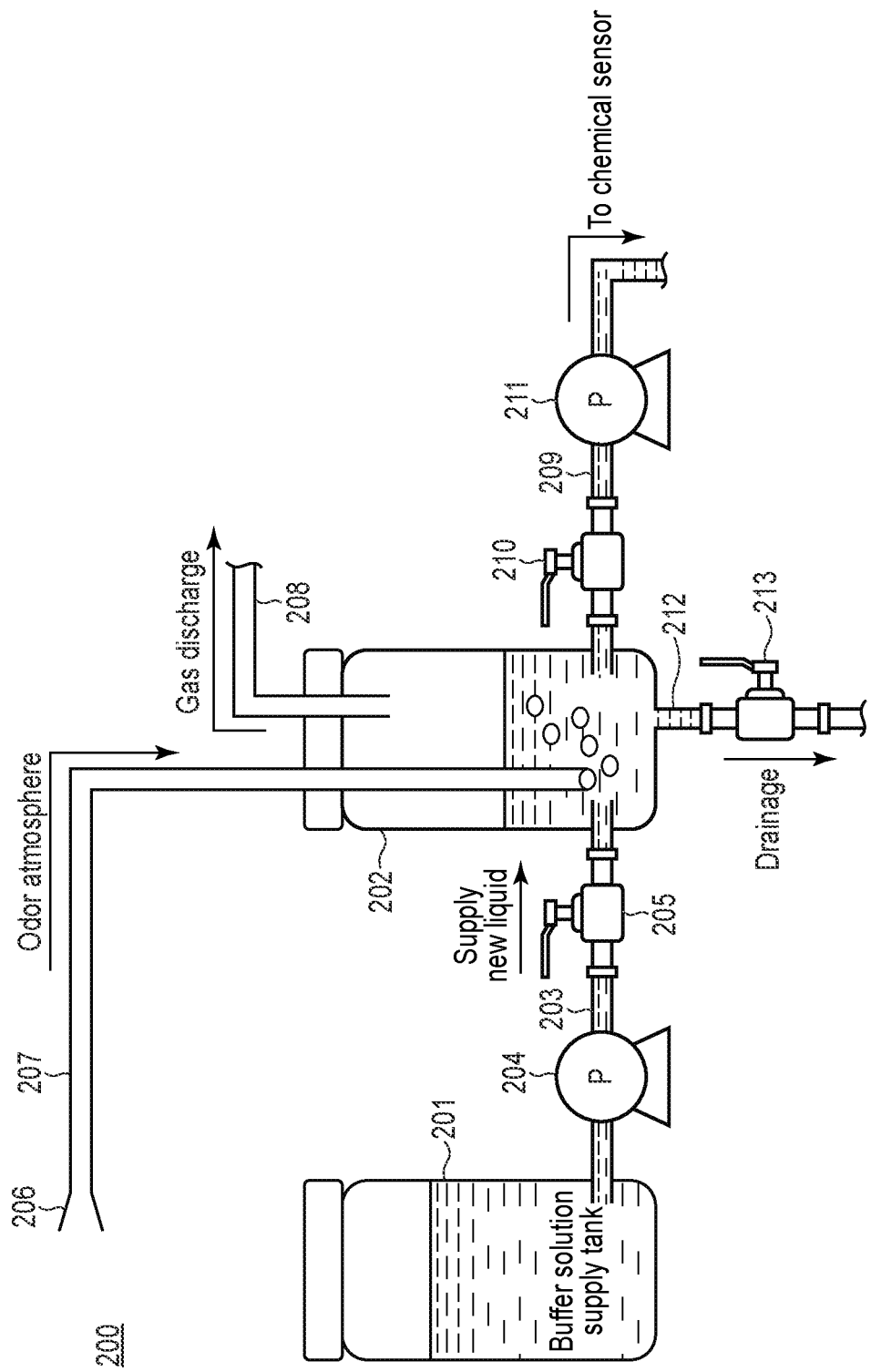
F I G. 15

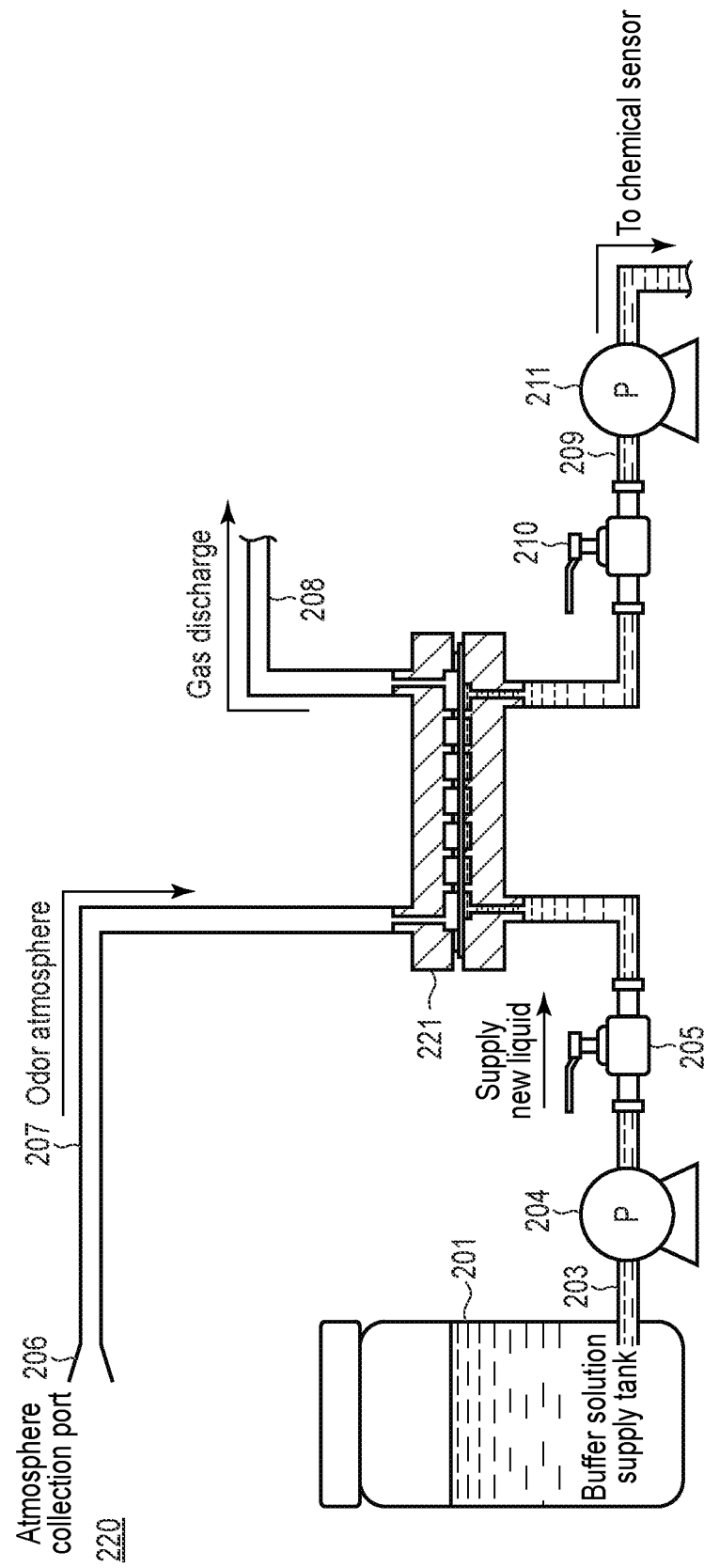
F I G. 16

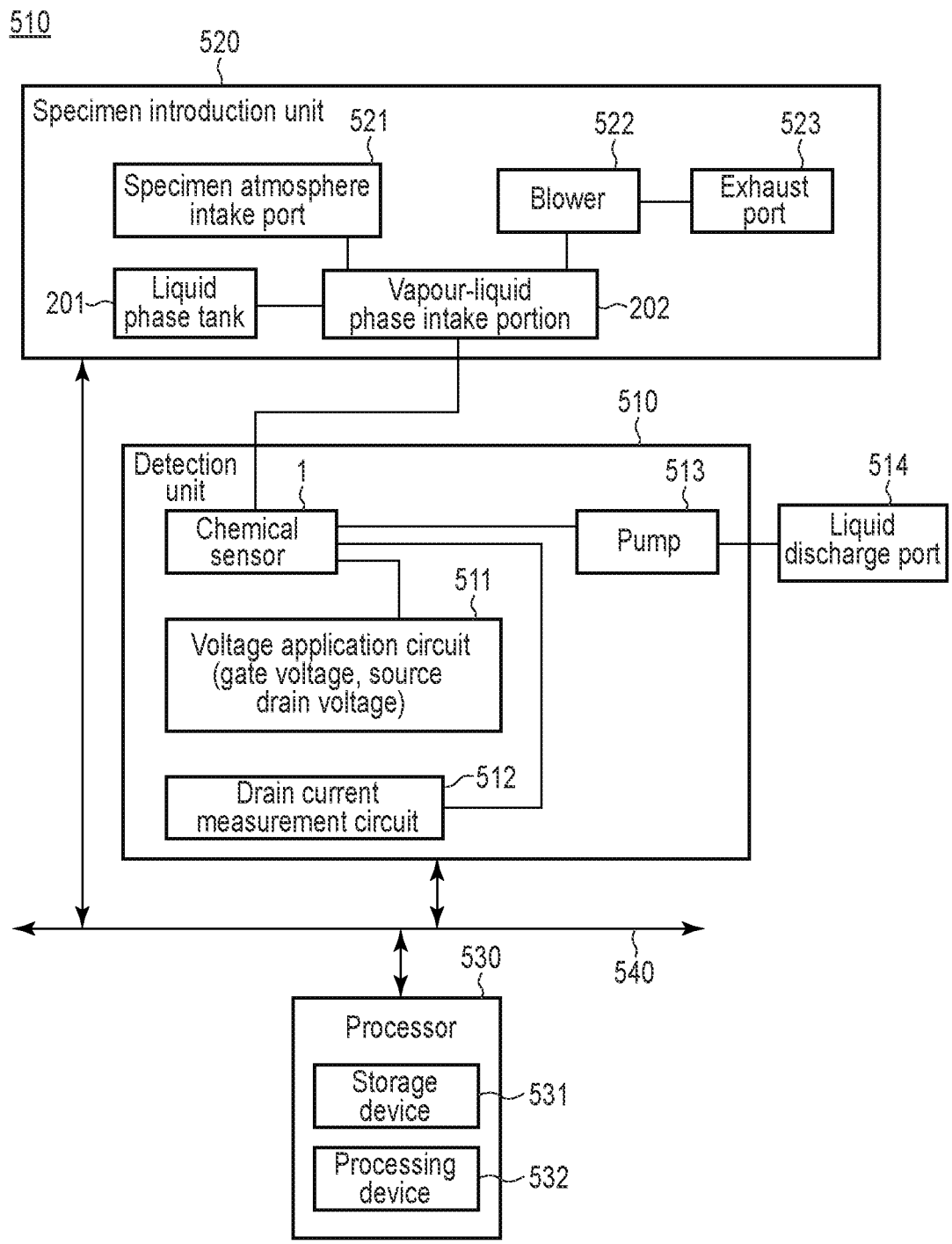
F I G. 20

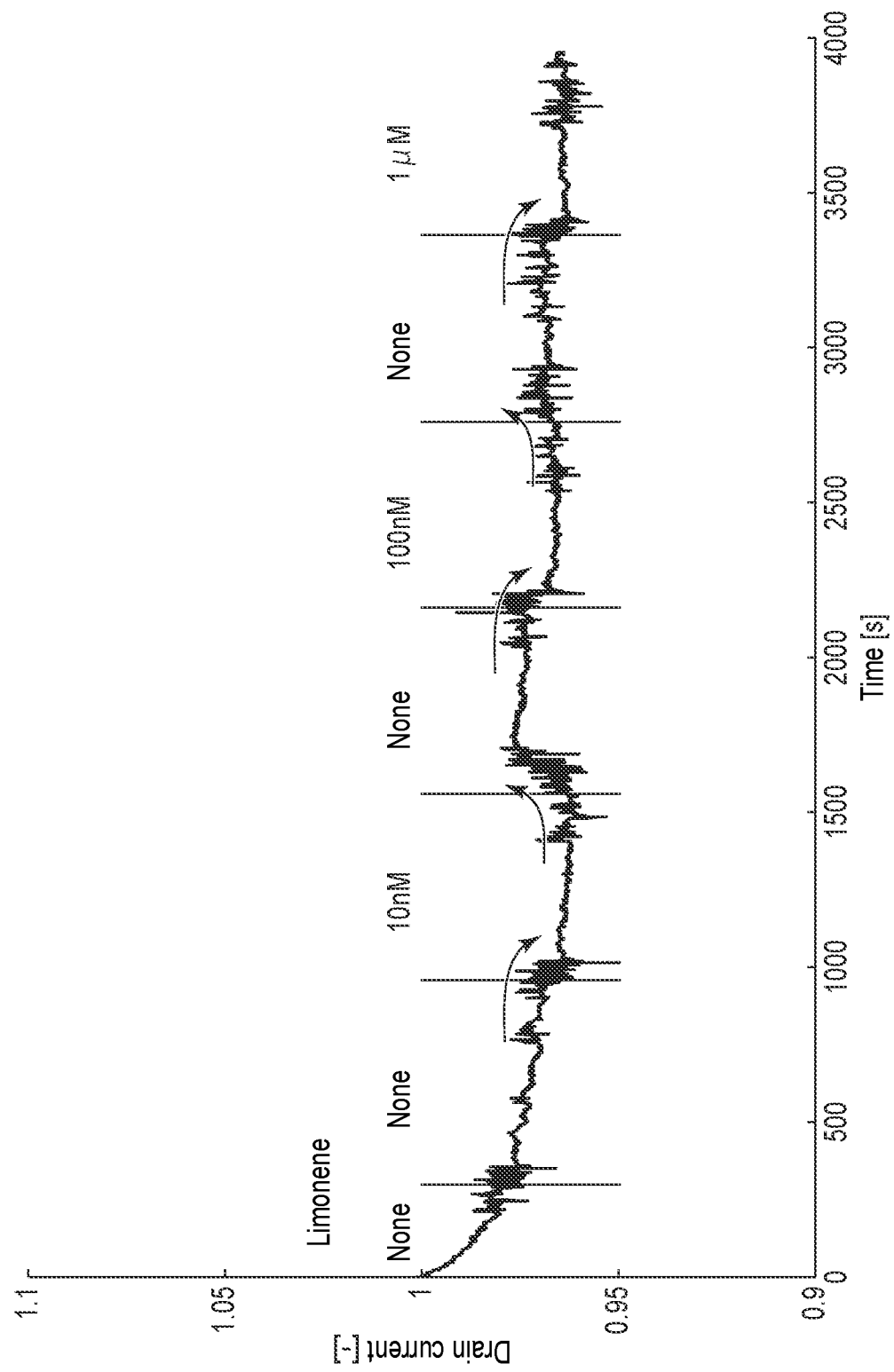
F I G. 21

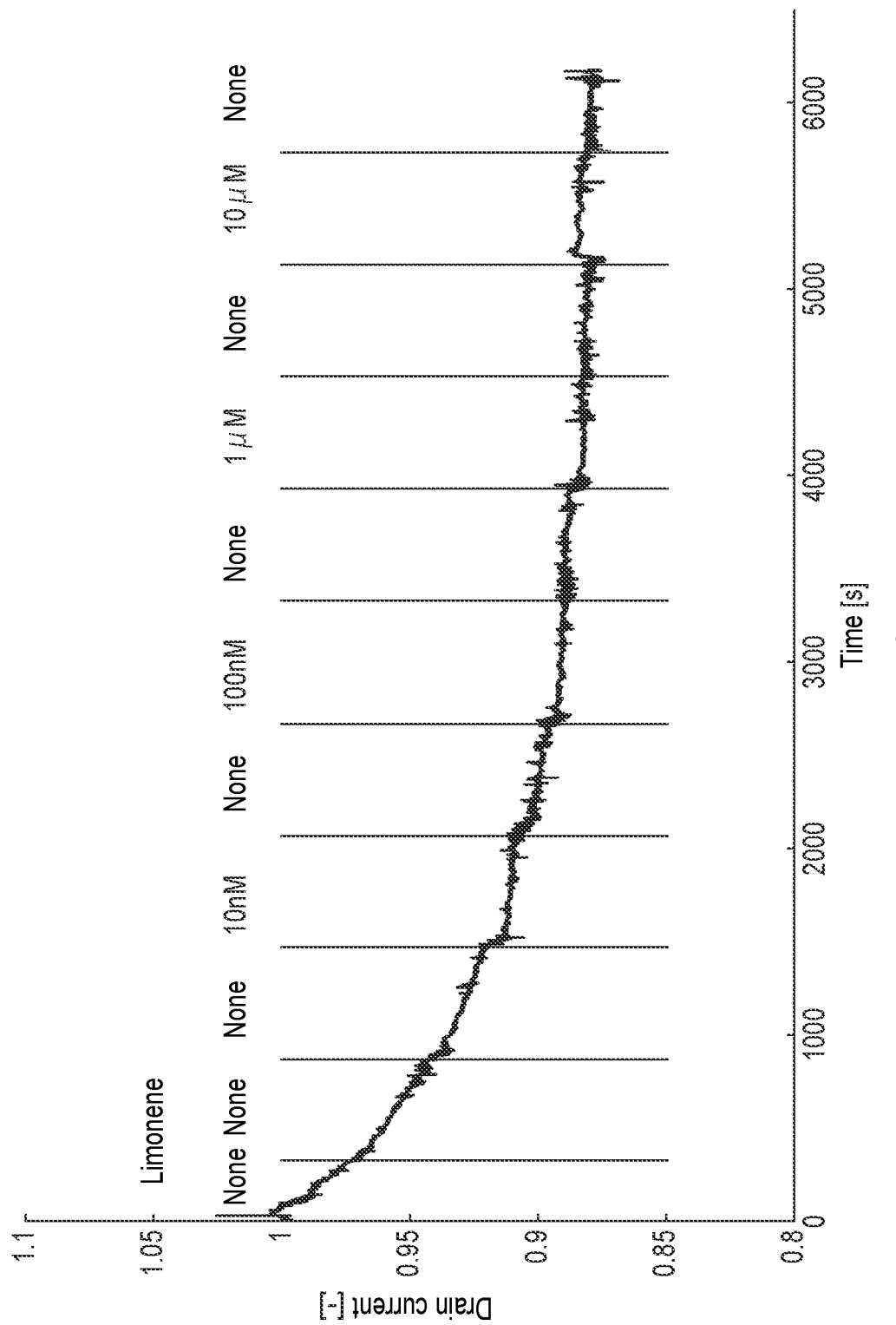
F I G. 22

SEQUENCE LISTING

```
<160> NUMBER OF SEQ ID NOS: 47

<210> SEQ ID NO 1
<211> LENGTH: 11
<212> TYPE: PRT
<213> ORGANISM: artificial
<220> FEATURE:
<223> OTHER INFORMATION: Fixing peptide

<400> SEQUENCE: 1

Gly Gly Gly Arg Gly Ala Gly Ala Gly Ala Arg
1               5                   10

<210> SEQ ID NO 2
<211> LENGTH: 11
<212> TYPE: PRT
<213> ORGANISM: artificial
<220> FEATURE:
<223> OTHER INFORMATION: Fixing peptide

<400> SEQUENCE: 2

Arg Gly Ala Gly Ala Gly Ala Arg Gly Gly Gly
1               5                   10
```

```
<210> SEQ ID NO 3
<211> LENGTH: 12
<212> TYPE: PRT
<213> ORGANISM: artificial
<220> FEATURE:
<223> OTHER INFORMATION: ECR peptide

<400> SEQUENCE: 3

Tyr Arg Ala Trp Gly Asn Ile Asp Glu Gly Cys Gly
1               5                   10

<210> SEQ ID NO 4
<211> LENGTH: 34
<212> TYPE: PRT
<213> ORGANISM: artificial
<220> FEATURE:
<223> OTHER INFORMATION: ECR peptide

<400> SEQUENCE: 4

Tyr Pro Leu Phe Thr Gly Thr Arg Ser Leu Pro Tyr Gly Met Phe Ile
1               5                   10                  15

Pro Gly Val Asn Asn Phe Lys Thr Pro Leu Tyr Gln Val Phe Phe Lys
            20                  25                  30

Cys Lys

<210> SEQ ID NO 5
<211> LENGTH: 14
<212> TYPE: PRT
<213> ORGANISM: artificial
<220> FEATURE:
<223> OTHER INFORMATION: ECR peptide

<400> SEQUENCE: 5

Phe Leu Leu Asn Ile Ile Glu Asn Pro Ala Gln Gly Cys Gly
1               5                   10

<210> SEQ ID NO 6
<211> LENGTH: 23
<212> TYPE: PRT
<213> ORGANISM: artificial
<220> FEATURE:
<223> OTHER INFORMATION: ECR peptide

<400> SEQUENCE: 6

Arg Gly Ala Gly Ala Gly Ala Arg Gly Gly Tyr Ser Tyr Phe Thr
1               5                   10                  15

Leu Leu Arg Arg Val Tyr Asn
            20

<210> SEQ ID NO 7
<211> LENGTH: 16
<212> TYPE: PRT
<213> ORGANISM: artificial
<220> FEATURE:
<223> OTHER INFORMATION: ECR peptide

<400> SEQUENCE: 7

Cys Gly Gly Gly Tyr Ser Tyr Phe Thr Leu Leu Arg Arg Val Tyr Asn
1               5                   10                  15

<210> SEQ ID NO 8
<211> LENGTH: 13
<212> TYPE: PRT
<213> ORGANISM: Drosophia malanogaster

<400> SEQUENCE: 8
```

Leu Leu Gln Ser Asn Ser Leu Glu Thr Phe Cys Glu Ser
1               5                   10

<210> SEQ ID NO 9
<211> LENGTH: 16
<212> TYPE: PRT
<213> ORGANISM: artificial
<220> FEATURE:
<223> OTHER INFORMATION: ECR peptide

<400> SEQUENCE: 9

Leu Leu Gln Ser Asn Ser Leu Glu Thr Phe Met Glu Ser Lys Cys Lys
1               5                   10                  15

<210> SEQ ID NO 10
<211> LENGTH: 16
<212> TYPE: PRT
<213> ORGANISM: artificial
<220> FEATURE:
<223> OTHER INFORMATION: ECR peptide

<400> SEQUENCE: 10

Leu Leu Gln Ser Asn Ser Leu Glu Thr Phe Ser Glu Ser Lys Cys Lys
1               5                   10                  15

<210> SEQ ID NO 11
<211> LENGTH: 25
<212> TYPE: PRT
<213> ORGANISM: Drosophia malanogaster

<400> SEQUENCE: 11

Ile Ser Ala Ser Ser Glu Pro Thr Leu Met Tyr Pro Thr Trp Ile Pro
1               5                   10                  15

Trp Asn Trp Arg Asp Ser Thr Ser Ala
            20                  25

<210> SEQ ID NO 12
<211> LENGTH: 28
<212> TYPE: PRT
<213> ORGANISM: artificial
<220> FEATURE:
<223> OTHER INFORMATION: ECR peptide

<400> SEQUENCE: 12

Ile Ser Ala Ser Ser Glu Pro Thr Leu Met Tyr Pro Thr Trp Ile Pro
1               5                   10                  15

Trp Asn Trp Arg Asp Ser Thr Ser Ala Lys Cys Lys
            20                  25

<210> SEQ ID NO 13
<211> LENGTH: 12
<212> TYPE: PRT
<213> ORGANISM: Drosophia malanogaster

<400> SEQUENCE: 13

Tyr Phe Leu Leu Phe Gly Asn Val Gly Ile Met Arg
1               5                   10

<210> SEQ ID NO 14
<211> LENGTH: 15
<212> TYPE: PRT
<213> ORGANISM: artificial
<220> FEATURE:
<223> OTHER INFORMATION: ECR peptide

```
<400> SEQUENCE: 14

Tyr Phe Leu Leu Phe Gly Asn Val Gly Ile Met Arg Lys Cys Lys
1               5                   10                  15

<210> SEQ ID NO 15
<211> LENGTH: 34
<212> TYPE: PRT
<213> ORGANISM: artificial
<220> FEATURE:
<223> OTHER INFORMATION: ECR peptide

<400> SEQUENCE: 15

Cys Gly Gly Gly Pro Ile Ser Met Lys Thr Phe Thr Val Met Ile Lys
1               5                   10                  15

Gly Ala Tyr Thr Met Lys Thr Leu Leu Asn Glu Ile Arg Lys Thr Gly
            20                  25                  30

Leu Glu

<210> SEQ ID NO 16
<211> LENGTH: 16
<212> TYPE: PRT
<213> ORGANISM: artificial
<220> FEATURE:
<223> OTHER INFORMATION: ECR peptide

<400> SEQUENCE: 16

Arg Ala Ala Gly Asn Phe Thr Asn Phe Leu Glu Leu Thr Lys Cys Lys
1               5                   10                  15

<210> SEQ ID NO 17
<211> LENGTH: 34
<212> TYPE: PRT
<213> ORGANISM: artificial
<220> FEATURE:
<223> OTHER INFORMATION: ECR peptide

<400> SEQUENCE: 17

Tyr Leu Met Ser Gly Val Leu Val Arg Glu Leu Pro Tyr Phe Met Trp
1               5                   10                  15

Tyr Trp Tyr Asp Trp His Arg Glu Gly Leu Tyr Glu Ile Thr Phe Phe
            20                  25                  30

Lys Cys

<210> SEQ ID NO 18
<211> LENGTH: 19
<212> TYPE: PRT
<213> ORGANISM: artificial
<220> FEATURE:
<223> OTHER INFORMATION: ECR peptide

<400> SEQUENCE: 18

Thr Ser Gln Ile Ser Ala Phe Asp Leu Phe Lys Phe Val Leu Phe Leu
1               5                   10                  15

Lys Cys Lys

<210> SEQ ID NO 19
<211> LENGTH: 17
<212> TYPE: PRT
<213> ORGANISM: artificial
<220> FEATURE:
<223> OTHER INFORMATION: ECR peptide

<400> SEQUENCE: 19
```

Met Ala Leu Gly Gly Gly Leu Leu Lys Thr Ile Tyr Asp Pro Ser Glu
1               5                   10                  15

Lys

<210> SEQ ID NO 20
<211> LENGTH: 25
<212> TYPE: PRT
<213> ORGANISM: artificial
<220> FEATURE:
<223> OTHER INFORMATION: ECR peptide

<400> SEQUENCE: 20

Met Ala Leu Arg Gly Ala Gly Ala Arg Gly Gly Leu Leu
1               5                   10                  15

Lys Thr Ile Tyr Asp Pro Ser Glu Lys
            20                  25

<210> SEQ ID NO 21
<211> LENGTH: 20
<212> TYPE: PRT
<213> ORGANISM: artificial
<220> FEATURE:
<223> OTHER INFORMATION: ECR peptide

<400> SEQUENCE: 21

Gly Leu Leu Lys Thr Arg Gly Lys Asn Leu Gly Thr Tyr Lys Tyr Leu
1               5                   10                  15

Met Gly Cys Gly
            20

<210> SEQ ID NO 22
<211> LENGTH: 19
<212> TYPE: PRT
<213> ORGANISM: artificial
<220> FEATURE:
<223> OTHER INFORMATION: ECR peptide

<400> SEQUENCE: 22

Gly Leu Leu Lys Thr Arg Gly Lys Asn Leu Gly Thr Tyr Lys Tyr Leu
1               5                   10                  15

Met Gly Cys

<210> SEQ ID NO 23
<211> LENGTH: 29
<212> TYPE: PRT
<213> ORGANISM: artificial
<220> FEATURE:
<223> OTHER INFORMATION: ECR peptide

<400> SEQUENCE: 23

Val His Phe Val Tyr Arg Tyr Phe Ala Thr Cys Lys Pro Asn Leu Leu
1               5                   10                  15

Arg Leu Phe Asn Leu Pro Thr Leu Leu Leu Trp Lys Lys
            20                  25

<210> SEQ ID NO 24
<211> LENGTH: 30
<212> TYPE: PRT
<213> ORGANISM: artificial
<220> FEATURE:
<223> OTHER INFORMATION: ECR peptide

<400> SEQUENCE: 24

Val His Phe Val Tyr Arg Tyr Phe Ala Thr Met Lys Pro Asn Leu Leu

```
                1               5                  10                 15
Arg Leu Phe Asn Leu Pro Thr Leu Leu Leu Trp Lys Cys Lys
                20                 25                 30

<210> SEQ ID NO 25
<211> LENGTH: 30
<212> TYPE: PRT
<213> ORGANISM: artificial
<220> FEATURE:
<223> OTHER INFORMATION: ECR peptide

<400> SEQUENCE: 25

Val His Phe Val Tyr Arg Tyr Phe Ala Thr Ser Lys Pro Asn Leu Leu
1               5                  10                 15
Arg Leu Phe Asn Leu Pro Thr Leu Leu Leu Trp Lys Cys Lys
                20                 25                 30

<210> SEQ ID NO 26
<211> LENGTH: 42
<212> TYPE: PRT
<213> ORGANISM: artificial
<220> FEATURE:
<223> OTHER INFORMATION: ECR peptide

<400> SEQUENCE: 26

Met Phe Tyr Cys Gly Tyr Ala Thr Trp Lys Thr Met Asn Glu His Lys
1               5                  10                 15
Asp Val Ser Asp Arg Thr Arg Ala Leu Gln Lys Gln Leu Phe Lys Ala
                20                 25                 30
Leu Val Leu Gln Thr Leu Ile Lys Cys Lys
            35                 40

<210> SEQ ID NO 27
<211> LENGTH: 35
<212> TYPE: PRT
<213> ORGANISM: artificial
<220> FEATURE:
<223> OTHER INFORMATION: ECR peptide

<400> SEQUENCE: 27

Gly Tyr Ala Thr Trp Lys Thr Met Asn Glu His Lys Asp Val Ser Asp
1               5                  10                 15
Arg Thr Arg Ala Leu Gln Lys Gln Leu Phe Lys Ala Leu Val Leu Gln
                20                 25                 30
Lys Cys Lys
        35

<210> SEQ ID NO 28
<211> LENGTH: 37
<212> TYPE: PRT
<213> ORGANISM: C.elegans

<400> SEQUENCE: 28

Leu Ile Ile Arg Asp Phe Arg Arg Thr Ile Phe Asn Phe Leu Cys Gly
1               5                  10                 15
Lys Lys Asn Ser Val Asp Glu Ser Arg Ser Thr Thr Arg Ala Asn Leu
                20                 25                 30
Ser Gln Val Pro Thr
        35

<210> SEQ ID NO 29
<211> LENGTH: 38
```

```
<212> TYPE: PRT
<213> ORGANISM: artificial
<220> FEATURE:
<223> OTHER INFORMATION: ECR peptide

<400> SEQUENCE: 29

Cys Leu Ile Ile Arg Asp Phe Arg Arg Thr Ile Phe Asn Phe Leu Met
1               5                   10                  15

Gly Lys Lys Asn Ser Val Asp Glu Ser Arg Ser Thr Thr Arg Ala Asn
            20                  25                  30

Leu Ser Gln Val Pro Thr
            35

<210> SEQ ID NO 30
<211> LENGTH: 38
<212> TYPE: PRT
<213> ORGANISM: artificial
<220> FEATURE:
<223> OTHER INFORMATION: ECR peptide

<400> SEQUENCE: 30

Cys Leu Ile Ile Arg Asp Phe Arg Arg Thr Ile Phe Asn Phe Leu Ser
1               5                   10                  15

Gly Lys Lys Asn Ser Val Asp Glu Ser Arg Ser Thr Thr Arg Ala Asn
            20                  25                  30

Leu Ser Gln Val Pro Thr
            35

<210> SEQ ID NO 31
<211> LENGTH: 23
<212> TYPE: PRT
<213> ORGANISM: C.elegans

<400> SEQUENCE: 31

Cys Gly Lys Lys Asn Ser Val Asp Glu Ser Arg Ser Thr Thr Arg Ala
1               5                   10                  15

Asn Leu Ser Gln Val Pro Thr
            20

<210> SEQ ID NO 32
<211> LENGTH: 22
<212> TYPE: PRT
<213> ORGANISM: C.elegans

<400> SEQUENCE: 32

Gly Lys Lys Asn Ser Val Asp Glu Ser Arg Ser Thr Thr Arg Ala Asn
1               5                   10                  15

Leu Ser Gln Val Pro Thr
            20

<210> SEQ ID NO 33
<211> LENGTH: 17
<212> TYPE: PRT
<213> ORGANISM: artificial
<220> FEATURE:
<223> OTHER INFORMATION: ECR peptide

<400> SEQUENCE: 33

Leu Ile Ile Arg Asp Phe Arg Arg Thr Ile Phe Asn Phe Leu Gly Cys
1               5                   10                  15

Gly
```

```
<210> SEQ ID NO 34
<211> LENGTH: 44
<212> TYPE: PRT
<213> ORGANISM: C.elegans

<400> SEQUENCE: 34

Ala Leu Thr His Thr Val Ala Met Ser Thr Leu Asn Phe Cys Gly Pro
1               5                   10                  15

Asn Val Ile Asn His Phe Tyr Cys Asp Leu Pro Gln Leu Phe Gln Leu
            20                  25                  30

Ser Cys Ser Ser Thr Gln Leu Asn Glu Leu Leu Leu
        35                  40

<210> SEQ ID NO 35
<211> LENGTH: 22
<212> TYPE: PRT
<213> ORGANISM: artificial
<220> FEATURE:
<223> OTHER INFORMATION: ECR peptide

<400> SEQUENCE: 35

Gly Pro Asn Val Ile Asn His Phe Tyr Met Asp Leu Pro Gln Leu Phe
1               5                   10                  15

Gln Leu Ser Gly Cys Gly
            20

<210> SEQ ID NO 36
<211> LENGTH: 28
<212> TYPE: PRT
<213> ORGANISM: artificial
<220> FEATURE:
<223> OTHER INFORMATION: ECR peptide

<400> SEQUENCE: 36

Ala Leu Thr His Thr Val Ala Met Ser Thr Leu Asn Phe Met Met Ser
1               5                   10                  15

Ser Thr Gln Leu Asn Glu Leu Leu Leu Gly Cys Gly
            20                  25

<210> SEQ ID NO 37
<211> LENGTH: 12
<212> TYPE: PRT
<213> ORGANISM: artificial
<220> FEATURE:
<223> OTHER INFORMATION: ECR peptide

<400> SEQUENCE: 37

Gly Pro Asn Val Ile Asn His Phe Tyr Gly Cys Gly
1               5                   10

<210> SEQ ID NO 38
<211> LENGTH: 38
<212> TYPE: PRT
<213> ORGANISM: artificial
<220> FEATURE:
<223> OTHER INFORMATION: ECR peptide

<400> SEQUENCE: 38

Ala Leu Thr His Thr Val Ala Met Ser Thr Leu Asn Phe Met Met Asp
1               5                   10                  15

Leu Pro Gln Leu Phe Gln Leu Ser Met Ser Ser Thr Gln Leu Asn Glu
            20                  25                  30

Leu Leu Leu Gly Cys Gly
        35
```

<210> SEQ ID NO 39
<211> LENGTH: 12
<212> TYPE: PRT
<213> ORGANISM: artificial
<220> FEATURE:
<223> OTHER INFORMATION: ECR peptide

<400> SEQUENCE: 39

Asp Leu Pro Gln Leu Phe Gln Leu Ser Gly Cys Gly
1               5                   10

<210> SEQ ID NO 40
<211> LENGTH: 38
<212> TYPE: PRT
<213> ORGANISM: artificial
<220> FEATURE:
<223> OTHER INFORMATION: ECR peptide

<400> SEQUENCE: 40

Ala Leu Thr His Thr Val Ala Met Ser Thr Leu Asn Phe Met Gly Pro
1               5                   10                  15

Asn Val Ile Asn His Phe Tyr Met Met Ser Ser Thr Gln Leu Asn Glu
            20                  25                  30

Leu Leu Leu Gly Cys Gly
        35

<210> SEQ ID NO 41
<211> LENGTH: 21
<212> TYPE: PRT
<213> ORGANISM: artificial
<220> FEATURE:
<223> OTHER INFORMATION: ECR peptide

<400> SEQUENCE: 41

Ala Leu Thr His Thr Val Ala Met Ser Thr Leu Asn Phe Met Met Gly
1               5                   10                  15

Gly Gly Gly Cys Gly
            20

<210> SEQ ID NO 42
<211> LENGTH: 38
<212> TYPE: PRT
<213> ORGANISM: artificial
<220> FEATURE:
<223> OTHER INFORMATION: ECR peptide

<400> SEQUENCE: 42

Gly Gly Gly Met Met Gly Pro Asn Val Ile Asn His Phe Tyr Met Asp
1               5                   10                  15

Leu Pro Gln Leu Phe Gln Leu Ser Met Ser Ser Thr Gln Leu Asn Glu
            20                  25                  30

Leu Leu Leu Gly Cys Gly
        35

<210> SEQ ID NO 43
<211> LENGTH: 31
<212> TYPE: PRT
<213> ORGANISM: artificial
<220> FEATURE:
<223> OTHER INFORMATION: ECR peptide

<400> SEQUENCE: 43

Ala Leu Thr His Thr Val Ala Met Ser Thr Leu Asn Phe Met Gly Pro

```
                1               5                  10                 15
Asn Val Ile Asn His Phe Tyr Met Met Gly Gly Gly Cys Gly
            20                  25                 30
```

<210> SEQ ID NO 44
<211> LENGTH: 28
<212> TYPE: PRT
<213> ORGANISM: artificial
<220> FEATURE:
<223> OTHER INFORMATION: ECR peptide

<400> SEQUENCE: 44

```
Gly Gly Gly Met Met Asp Leu Pro Gln Leu Phe Gln Leu Ser Met Ser
1               5                   10                  15
Ser Thr Gln Leu Asn Glu Leu Leu Leu Gly Cys Gly
            20                  25
```

<210> SEQ ID NO 45
<211> LENGTH: 41
<212> TYPE: PRT
<213> ORGANISM: artificial
<220> FEATURE:
<223> OTHER INFORMATION: ECR peptide

<400> SEQUENCE: 45

```
Ala Leu Thr His Thr Val Ala Met Ser Thr Leu Asn Phe Met Gly Pro
1               5                   10                  15
Asn Val Ile Asn His Phe Tyr Met Asp Leu Pro Gln Leu Phe Gln Leu
            20                  25                  30
Ser Met Met Gly Gly Gly Gly Cys Gly
        35                  40
```

<210> SEQ ID NO 46
<211> LENGTH: 18
<212> TYPE: PRT
<213> ORGANISM: artificial
<220> FEATURE:
<223> OTHER INFORMATION: ECR peptide

<400> SEQUENCE: 46

```
Gly Gly Gly Met Met Ser Ser Thr Gln Leu Asn Glu Leu Leu Leu Gly
1               5                   10                  15
Cys Gly
```

<210> SEQ ID NO 47
<211> LENGTH: 14
<212> TYPE: PRT
<213> ORGANISM: artificial
<220> FEATURE:
<223> OTHER INFORMATION: Fixing peptide

<400> SEQUENCE: 47

```
Gly Gly Gly Arg Gly Ala Gly Ala Gly Ala Arg Gly Gly Gly
1               5                   10
```

CHEMICAL SENSOR, METHOD FOR DETECTING TARGET SUBSTANCE, AND APPARATUS FOR DETECTING THE SAME

CROSS-REFERENCE TO RELATED APPLICATIONS

This application is based upon and claims the benefit of priority from Japanese Patent Application No. 2021-044802, filed Mar. 18, 2021, the entire contents of which are incorporated herein by reference.

REFERENCE TO AN ELECTRONIC SEQUENCE LISTING

The sequence listing is entitled "Sequence Listing '880 Application" and is associated with U.S. application Ser. No. 17/470,880, entitled "CHEMICAL SENSOR, METHOD FOR DETECTING TARGET SUBSTANCE, AND APPARATUS FOR DETECTING THE SAME." The sequence listing was created on Dec. 7, 2021 and is 14,697 bytes in size. The contents of the electronic sequence listing are herein incorporated by reference in their entirety.

FIELD

Embodiments described herein relate generally to a chemical sensor, a method for detecting a target substance, and an apparatus for detecting the same.

BACKGROUND

Devices capable of detecting chemical substances are considered to be useful in fields such as detection of biological information and detection of harmful substances in the air. In particular, it is difficult to specifically and sensitively detect small molecules because many similar substances exist. In such a situation, a chemical sensor capable of specifically and highly sensitively detecting a chemical substance is required.

BRIEF DESCRIPTION OF THE DRAWINGS

FIG. 5 is a diagram illustrating an example of a method for immobilizing a first ECR peptide of the chemical sensor of the embodiment.

FIG. 6 is a diagram illustrating an example of a dimer of the first ECR peptide of the embodiment.

FIG. 7 is a diagram illustrating an example of an amino acid sequence of the extracellular region used for the first ECR peptide or a second ECR peptide of the embodiment.

FIG. 8 is a diagram illustrating art example of an amino acid sequence of the extracellular region used for the first ECR peptide or a second ECR peptide of the embodiment.

FIG. 9 is a diagram illustrating an example of an amino acid sequence of the extracellular region used for the first ECR peptide or a second ECR peptide of the embodiment.

FIG. 11A is a cross-sectional view illustrating an example of a chemical sensor using two extracellular regions for the first ECR peptide of the embodiment.

FIG. 11B is an enlarged view of the first ECR peptide or the second ECR peptide.

FIG. 11C is a table indicating a combination of the first ECR peptide or the second ECR peptide.

FIG. 12A is a cross-sectional view illustrating an example of a chemical sensor using two extracellular regions for the second ECR peptide of the embodiment.

FIG. 12B is an enlarged view of the first ECR peptide or the second ECR peptide.

FIG. 12C is a table indicating a combination of the first ECR peptide or the second ECR peptide.

FIG. 15 is a diagram illustrating an example of a specimen intake device of the embodiment.

FIG. 16 is a diagram illustrating an example of a specimen intake device of the embodiment.

FIG. 20 is a block diagram illustrating an example of a detecting apparatus according to an embodiment.

FIG. 21 is a graph illustrating experimental results of Example 1.

FIG. 22 is a graph illustrating experimental results of Comparative Example 3.

DETAILED DESCRIPTION

In general, according to one embodiment, a problem to be solved is to provide a chemical sensor, a method for detecting a target substance, and apparatus for detecting the same which can specifically and sensitively detect small molecules.

A chemical sensor according to one embodiment detects a target substance in a specimen. The chemical sensor comprises a sensitive film, a first extracellular region peptide of a transmembrane receptor immobilized on the sensitive film, a liquid phase disposed on the sensitive film, and a second extracellular region peptide of the transmembrane receptor contained within the liquid phase. Hereinafter, embodiments will be described with reference to the accompanying drawings. Note that, in each embodiment, substantially the same constituent parts are denoted by the same reference signs and an explanation thereof will be partly omitted in some cases. The drawings are schematic, and a relation of thickness and planer dimension of each part, a thickness ratio among parts, and so on are sometimes different from actual ones.

Chemical Sensor

Figure 1:
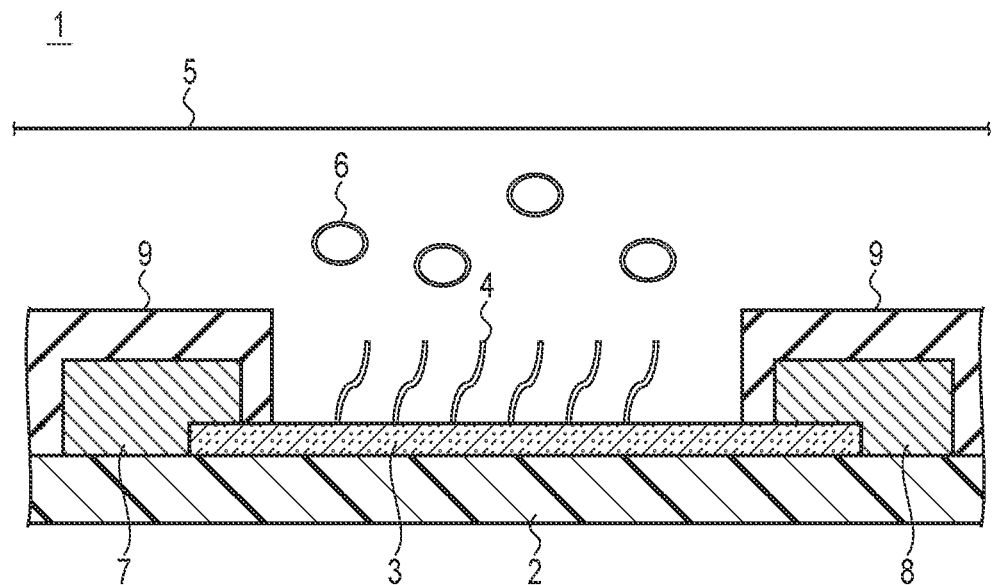
FIG. 1 is a cross-sectional view illustrating an example of a chemical sensor according to an embodiment.

A chemical sensor of an embodiment is a sensor for detecting a target substance. As illustrated in FIG. 1, a chemical sensor 1 of the embodiment includes a substrate 2 and a sensitive film 3 disposed on a surface of the substrate 2. A first extracellular region (ECR) peptide 4 of the transmembrane receptor is immobilized on the surface of the sensitive film 3 opposite to the substrate 2. A liquid phase 5 is disposed on the sensitive film 3, and a second ECR peptide 6 of the transmembrane receptor is present in the liquid phase 5. In the present specification, the term "immobilizing" includes not only a case of being directly immobilized to the sensitive film 3 but also a case of being indirectly immobilized via another substance. The term "immobilized" also includes, for example, a state of being adsorbed to or attracted to the sensitive film 3 without chemical bonding or the like.

Figure 2:
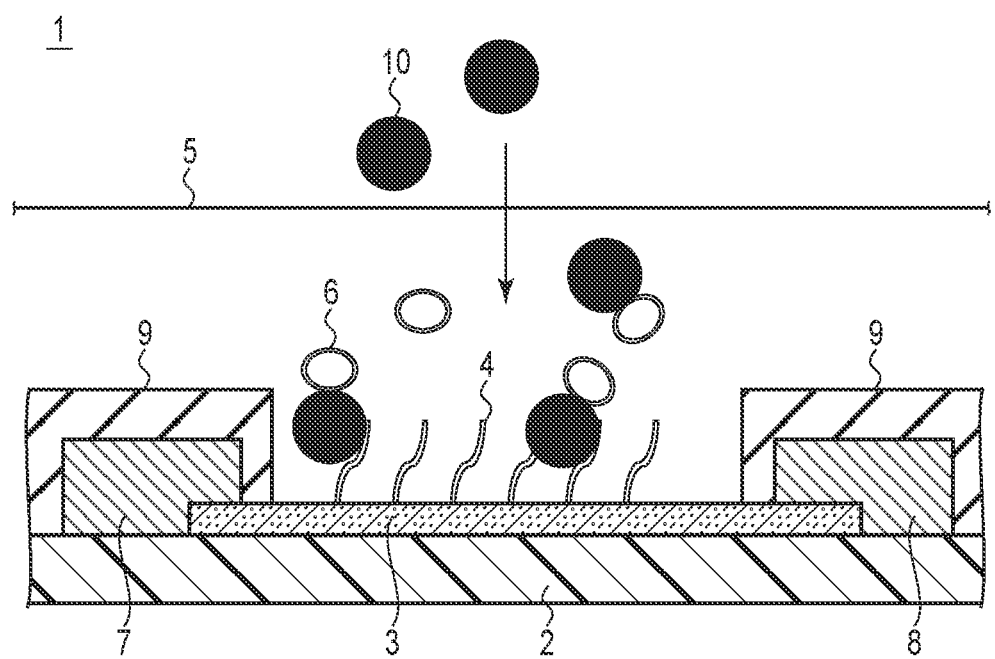
FIG. 2 is a cross-sectional view illustrating a state when the chemical sensor of the embodiment is used.

The first ECR peptide 4 and the second ECR peptide 6 are derived from the same transmembrane receptor and the target substance 10 is a ligand for this transmembrane receptor. In the chemical sensor 1, as illustrated in FIG. 2, the target substance 10 is taken into the liquid phase 5, the second ECR peptide 6 present in the liquid phase 5 is bonded to the target substance 10, and the target substance 10 is captured by the first ECR peptide 4 immobilized on the sensitive film 3. As a result, the target substance 10 is bonded to the sensitive film 3 in an open sandwich state sandwiched between two ECR peptides.

For example, the chemical sensor 1 includes a mechanism for detecting a change in physical properties, for example, electric resistance, of the sensitive film 3 that occurs when the target substance 10 is bonded to the sensitive film 3. For example, as illustrated in FIG. 1, the chemical sensor 1 has a configuration of a field effect transistor (FET) further including a first electrode 7 (source electrode) electrically connected to one end of the sensitive film 3, a second electrode 8 (drain electrode) electrically connected to the other end of the sensitive film 3, and an insulator 9 covering the two electrodes. In this case, it is preferable that the sensitive film 3 has a configuration of a graphene FET formed of graphene capable of detecting with higher sensitivity. For example, although not illustrated, the chemical sensor 1 further includes a circuit including a gate electrode and a power supply for applying a gate voltage, and a circuit including an ammeter for measuring a drain current value obtained from the first electrode 7 and the second electrode 8, and the first electrode 7 and the second electrode 8 can be connected to these circuits, respectively. These circuits can be arranged in the substrate 2, for example.

Hereinafter, specific examples of the first ECR peptide and the second ECR peptide will be described.

The transmembrane receptor from which the first ECR peptide 4 and the second ECR peptide 6 are derived is a transmembrane protein which is activated by being stimulated by bonding of a signal molecule (ligand) to the extracellular region, and transmits a signal into a cell, for example, as necessary. The transmembrane receptor has a plurality of extracellular regions. The transmembrane receptor is, for example, a G protein-coupled receptor such as an olfactory receptor. For example, the transmembrane receptors expressed in animals can be used. The animal is, for example, a vertebrate, an insect, or the like, and is, for example, a human, a fly, a mosquito, a mouse, a rat, a rabbit, a cow, a dog, or the like.

The first ECR peptide 4 and the second ECR peptide 6 are polypeptides including at least a part of amino acid sequence of the mutually different extracellular regions of the transmembrane receptor.

Figure 3:
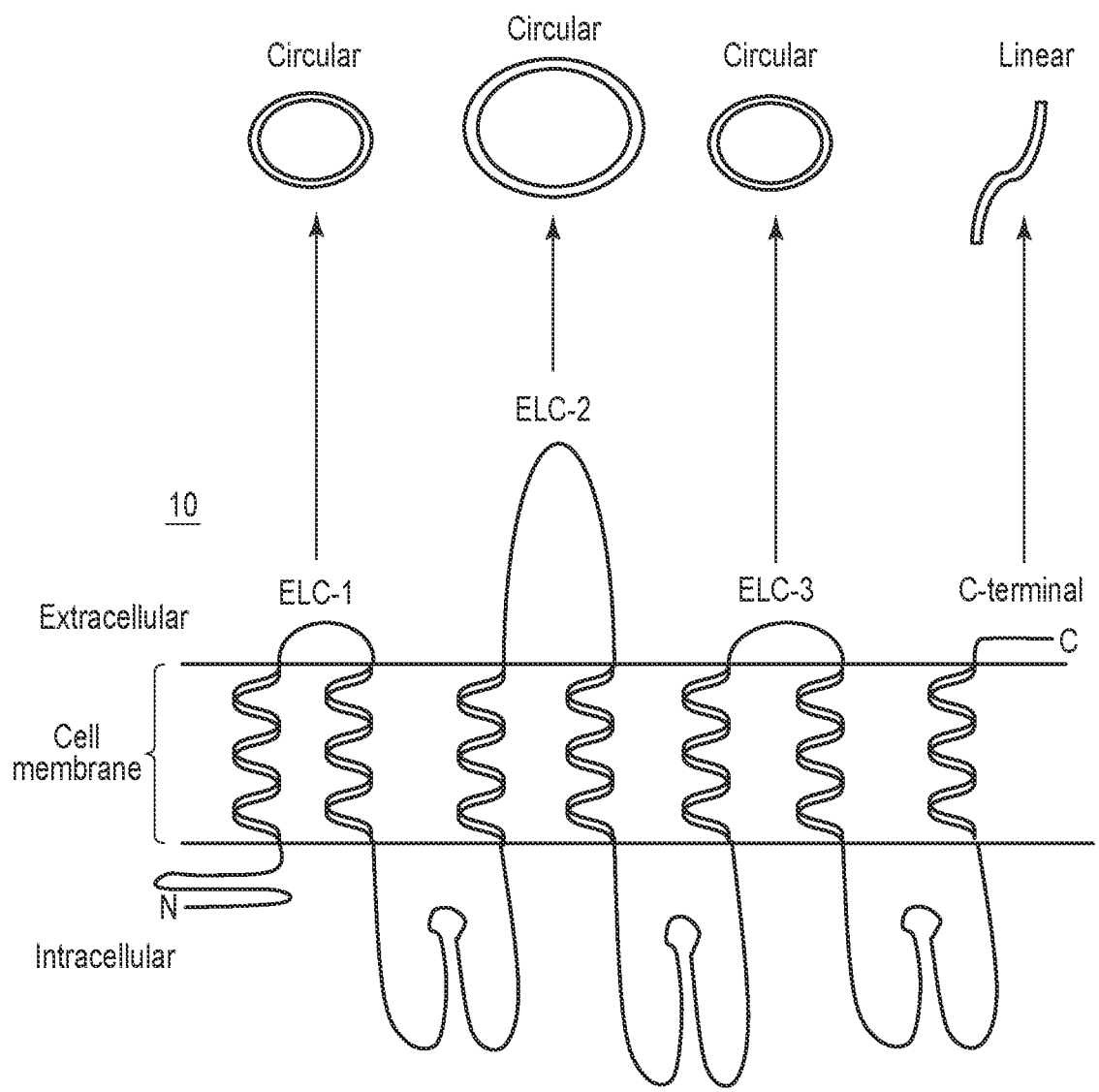
FIG. 3 is a diagram illustrating an example of a transmembrane receptor of the embodiment and an extracellular region thereof.

For example, a 7-transmembrane receptor 11 illustrated in FIG. 3 has 3 extracellular loops (ECL): ECL-1, ECL-2, and ECL-3, and 4 extracellular regions of 1 extracellular C-terminal. When ECL is used, it is preferable to circularize the amino acid sequence in order to reproduce the original shape of the transmembrane receptor as much as possible. When an extracellular terminal (here, an extracellular C-terminal) is used, it is preferable to use it in a linear form. It is also possible to use a transmembrane receptor having an extracellular N-terminal, and in that case, it is preferable to use the extracellular N-terminal as a linear form.

Figure 4A:
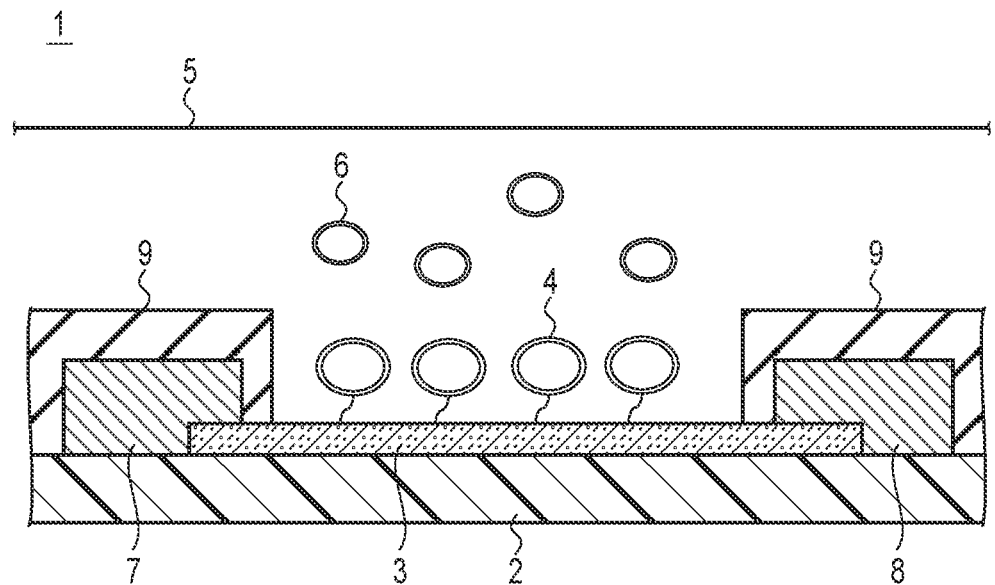
FIGS. 4A and 4B are cross-sectional views illustrating examples of the chemical sensor according to the embodiment.
Figure 4B:
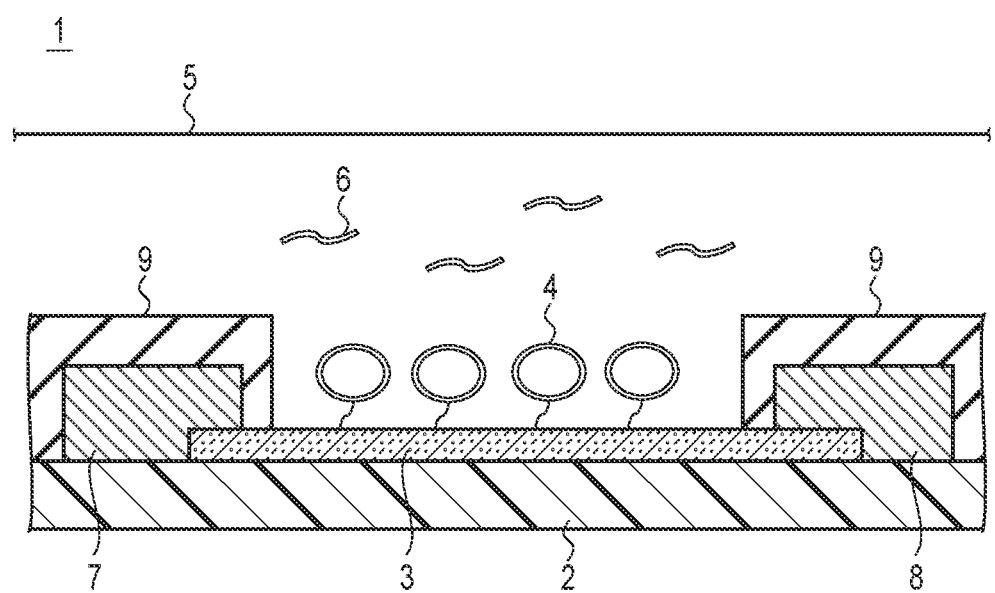

For example, the extracellular terminal may be used for the first ECR peptide 4 and any of the ECLs may be used for the second ECR peptide 6 as illustrated in FIG. 1, any of the ECLs may be used for the first ECR peptide 4 and any of the ECLs may be used for the second ECR peptide 6 as illustrated in FIG. 4A, or any of the ECLs may be used for the first ECR peptide 4 and the extracellular terminal may be used for the second ECR peptide 6 as illustrated in FIG. 4B. Although not shown, if an extracellular N-terminal and an extracellular C-terminal are present, one may be used for the first ECR peptide 4 and the other for the second ECR peptide 6.

When used as the first ECR peptide 4 and the second ECR peptide 6, it is not necessary to use the full length of the amino acid sequence of the selected extracellular region, and a part of the amino acid sequence may be used as long as the bonding ability with a ligand is not adversely affected. For example, the amino acid sequence length of the extracellular region used for the first ECR peptide 4 is, for example, 3 mer or more and less than 50 mer, and preferably 5 mer or more and 40 mer or less. The amino acid sequence length of the extracellular region used for the second ECR peptide 6 is, for example, 3 mer or more and less than 50 mer, and preferably 5 mer or more and 40 mer or less. In addition, as long as the bonding ability with a ligand is not adversely affected, it is also possible to modify and use some amino acids in the amino acid sequence of the extracellular region, such as deletion, substitution, or insertion. For example, as will be described in detail later, it is preferable to appropriately insert and substitute an amino acid when immobilizing to the sensitive film 3 or when using in the liquid phase 5. The modification is appropriately performed according to various other reasons such as adjustment of water solubility, label modification, and adjustment of affinity.

The method for immobilizing the first ECR peptide 4 on the sensitive film 3 is not limited, but the first. ECR peptide 4 of the transmembrane receptor can be immobilized on the sensitive film 3 by adding a modifying group to the first ECR peptide 4 and/or the sensitive film 3 and chemically synthesizing the both. When the sensitive film 3 is graphene, it is preferable to immobilize the sensitive film 3 via polyaromatic such as pyrene which is easily adsorbed to graphene. Alternatively, it is preferable to immobilize via an immobilizing peptide containing a peptide that forms a β-sheet structure easily adsorbed to graphene. The peptide forming the β sheet structure is not limited, but for example, it is preferable to use a sequence in which G (glycine) and A (alanine) are repeated a plurality of times (for example, GAGAGA or AGAGAG), a peptide containing V (valine), Y (tyrosine), and I (isoleucine), or the like. An amino acid having a conjugated double bond in a side chain, that is, R (arginine), Y (tyrosine), F (phenylalanine), W (tryptophan), or the like is preferably disposed at both ends of these peptides. The conjugated double bonds contained in the side chains of these amino acids are attracted to graphene by an interaction, and thus serve as anchors and are more strongly immobilized to graphene. Among them, since R is hydrophilic, the peptide is easily water-soluble and easy to handle. The immobilizing peptide preferably further contains GGG between the first ECR peptide 4 and the peptide forming a β-sheet structure. As a result, when the first ECR peptide 4 is immobilized to the sensitive film 3, the first ECR peptide 4 can be moved more flexibly and easily bonded to the target, substance 10.

Preferable examples of the immobilizing peptide are peptides of the following SEQ ID NO: 1 or SEQ ID NO: 2:

GGG-RGAGAGAR (SEQ ID NO: 1)

RGAGAGAR-GGG. (SEQ ID NO: 2)

When the extracellular terminal is used for the first ECR peptide 4, for example, a linear sequence in which the amino acid sequence of the extracellular terminal is connected to the N-terminal (GGG side) of the immobilizing peptide may be synthesized.

When any one of ECL is used for the first ECR peptide 4, a cyclic peptide containing ECL to which an immobilizing peptide is added may be synthesized, but this is often difficult. In that case, as illustrated in FIG. 5, the immobilizing peptide to which a binder such as maleimide (such as 3-maleimidopropancyl, Mal) is added at the N-terminal (GGG side) is first prepared, the immobilizing peptide is first bound to the sensitive film 3 (part (a) of FIG. 5), and the first ECR peptide 4 is added thereto so as to bond the first ECR peptide 4 to the immobilizing peptide via the binder (part (b) of FIG. 5).

When maleimide is used, a thiol group of C (cysteine) contained in the first ECR peptide 4 is bonded to maleimide, whereby the first ECR peptide 4 is immobilized on the sequence of SEQ ID NO: 1 or SEQ ID NO: 2. It is preferable that the amino acid sequence to be used as the first ECR peptide 4 is selected so that C is placed at the end, or when the amino acid sequence to be used does not contain C, C is inserted into a cyclic joint. At that time, KCK (K is lysine), GC, GCG, or the like may be inserted. When the sequence of KCK is inserted, the water solubility of the first ECR peptide 4 is increased, so that it is easy to adjust the aqueous solution when reacting with the immobilizing peptide. When the sequence of GC or GCG is inserted, since G has only hydrogen in the side chair, the risk of causing an unexpected inhibitory effect or the like on the ligand bonding ability of the ECR peptide in the transmembrane receptor is reduced. At this time, in a case where C is present in the middle of the sequence of the first ECR peptide A, when it is bonded to maleimide, the region that is bonded to the target substance 10 faces the sensitive film 3 side, and there is a possibility that the efficiency of capturing the target substance 10 is reduced. Therefore, in such a case, C is preferably substituted with M (methionine) having the same sulfur atom, S (serine) in which a sulfur atom is substituted with an oxygen atom, or the like.

The binder is not limited to maleimide, and N-Hydroxysuccinimide (NHS) may be used. When NHS is used, K (lysine) is bound. Therefore, similarly, when the sequence of the first ECR peptide 4 does not contain K, it is preferable to insert K into the joint of the rings, and when K is present in the middle of the sequence, it is preferable to substitute it with R (arginine) or the like having the same positive charge.

The immobilizing of the first ECR peptide 4 on the sensitive film 3 illustrated in parts (a) and (b) of FIG. 5 can be performed by the following procedure. First, when there is a liquid on the sensitive film 3, the liquid is substituted with pure water, and then the pure water is substituted with a solution (aqueous solution) containing the immobilizing peptide. Thereafter, when the membrane is left for about 1 hour, a self-assembled membrane of the immobilizing peptide is formed on the sensitive film 3. Next, the liquid on the sensitive film 3 is substituted with pure water to remove the excess the immobilizing peptide, and then the pure water is substituted with a solution containing the first ECR peptide 4 (for example, containing 0.5% DMSO aqueous solution, 50 μM TCEP). Thereafter, by leaving it overnight, the maleinide and the thiol contained in C of the first ECR peptide 4 are bound, and the first ECR peptide 4 can be immobilized on the sensitive film 3.

For the second ECR peptide 6, in the case of using any of ECL, it is not always necessary to insert C, K, or the like when forming the second ECR peptide 6 into a cyclic form. However, it is preferable that C is present at the annular joint. In this case, as illustrated in FIG. 6, two second ECR peptides 6 can form a disulfide bond at C to form a dimer. In such a dimer, since the region to which the target substance 10 is bonded is exposed to the outside, the target substance 10 is easily captured, and the detection sensitivity can be improved. The amino sequence used for the second ECR peptide 6 can be selected such that C is disposed at the end, or such a dimer can be formed by inserting C into the joint.

In addition, the first ECR peptide 4 and the second ECR peptide 6 may contain an amino acid sequence classified into a transmembrane region as necessary. For example, in some transmembrane receptors, the ligand penetrates into the transmembrane region and is bonded, and in this case, if a specific sequence of the transmembrane region is removed or modified, the ligand may not be bonded. For example, such a region is often located in the vicinity of the boundary with the extracellular region. When such a transmembrane receptor is used, it is preferable to use a sequence including the region for the first ECR peptide 4 and/or the second ECR peptide 6.

FIGS. 7 to 9 and Table 1 below illustrate examples of preferable extracellular region sequences for four transmembrane receptors. The transmembrane receptors exemplified herein are CquiOR10 which is an olfactory receptor for skatol present in a mosquito (Culex quinquefasciatus), OR19a which is an olfactory receptor for odor components such as valencene and limonene present in Drosophila melanogaster, CqOr118 which is an olfactory receptor for R body of octenol present in a mosquito (Culex quinquefasciatus), and Odr10 which is an olfactory receptor for diacetyl present in a nematode (C. elegans). In the drawings and the tables, underlines indicate artificially inserted amino acids, and bold letters indicate substituted amino acids.

TABLE 1

| | | | SEQ ID NO: |
|---|---|---|---|
| CquiOR10 | | | |
| ECL-1 | | YRAWGNIDE-GCG (Circularized) | 3 |
| ECL-2 | | YPLFTGTRSLPYGMFIPGVNNKTPLYQVFF-KCK (Circularized) | 4 |
| ECL-3 | | FLLNIIENPAQ-CCG (Circularized) | 5 |
| Extracellular | (a) | RGAGAGARGGG-YSYFTLLRRVYN | 6 |
| C-terminal | (b) | CGGG-YSYFTLLRRVYN | 7 |
| OR19a | | | |
| ECL-1 | (a) | LLQSNSLETFCES | 8 |
| | (b) | LLQSNSLETFMES-KCK (Circularized) | 9 |
| | (c) | LLQSNSLETFSES-KCK (Circularized) | 10 |
| ECL-2 | (a) | ISASSEPTLMYPTWIPWNWRDSTSA (Circularized) | 11 |
| | (b) | ISASSEPTLMYPTWIPWNWRDSTSA-KCK (Circularized) | 12 |
| | (a) | YFLLFGNVGIMR (Circularized) | 13 |
| | (b) | YFLLYGNVGIMR-KCK (Circularized) | 14 |
| Extracellular C-(terminal) | | CGGGPIS MHTFTVMIKG AYTMKTLLNEIRKTGLE | 15 |
| CqOr118 | | | |
| ECL-1 | | RAAGNFTNFLELT-KCK (Circularized) | 16 |
| ECL-2 | | YLMSGVLVRELPYFMWYWYDWHREGLYEITFF-KC (Circularized) | 17 |
| ECL-3 | | TSQISAFDLFKFVULFL-KCK (Circularized) | 18 |
| Extracellular | (a) | Mal-GGG-LLKTIYDPSEK | 19 |
| C-terminal | (b) | Mal-RGAGAGARGGG-LLKTIYDPSEK | 20 |
| Odr10 | | | |
| ECL-1 | (a) | GLLKTRGKNLGTYKYLM-GCG (Circularized) | 21 |
| | (b) | GLLKTRCKNLGTYKYLM-GC (Circularized) | 22 |
| ECL-2 | (a) | VHFVYRYFATCKPNLLRLFNLPTLLLW-KK (Circularized) | 23 |
| | (b) | VHFVYRYFATMKPNLLRLFNLPTLLLW-KGK (Circularized) | 24 |
| | (c) | VHFVYRYFATSKPNLLRLFNLPTLLLN-KCK (Circularized) | 25 |
| ECL-3 | (a) | MFYCGYATWKTMNEHKDVSDRTRALQKQLFKALVLQTLI-KCK (Circularized) | 26 |
| | (b) | GYATWKTMNEHKDVSDRTRALQKQLFKALVLQ-KCK (Circularized) | 27 |
| Extracellular | (a) | LIIRDFRRTIFNFLCGKKNSVDESRSTTRANLSQVPT | 28 |
| C-terminal | (b) | CLIIRDFRRTIFNFLMGKKNSVDESRSTTRANLSQVPT | 29 |
| | (c) | CLIIRDERRTIFNFLSGKKNSVDESRSTTRANLSQVPT | 30 |
| | (d) | CGKKNSVDFSRSTTRANLSQVPT | 31 |
| | (e) | Mal-GKKNSVDESRSTTRANLSQVPT | 32 |
| | (f) | LIIRDFRRTIFNFL-GCG (Circularized) | 33 |

The sequence to be added is not limited to the above, and may be changed according to the application. In addition, all the peptides described as cyclized in the above table are cyclized by connecting the N-terminal and the C-terminal.

The ECL-1 of OR19a described above is preferably used for the first ECR peptide 4. The ECL-2 is preferably used for the second ECR peptide 6.

(a) of ECL-2 of the Odr10 described above is preferably used for second ECR peptide 6. The sequence VHFV of N-terminal of (a) is a sequence contained in the transmembrane region, but is a sequence that is not bonded to diacetyl as a ligand when modified, and it is known that LLLW of the C-teminal is also a sequence contained in the transmembrane region, but is not bonded to diacetyl when removed. Therefore, it is preferable to use a sequence including these. Since (a) of ECL-3 is 40 mer and is difficult to synthesize, it is more preferable to use (b). (a) of the extracellular C-terminal is preferably used for the second ECR peptide 6, but since it contains C in the middle, it is preferable to substitute it with M and add C to the terminal as in (b), or substitute it with S and add C to the terminal as in (c). In addition, C in the middle of the extracellular C-teminal can form a disulfide bond with C at the base of ECL3. In this case, the N-terminal side of the extracellular C-terminal from C forms a loop as in (f), and the C-terminal side from C is a linear chain as in (d) or (e). Here, when (d) and (f) are mixed and used, the maleimide of (a) can be bonded to C of (f) to have a structure equivalent to that when C in the middle of the extracellular C-terminal forms a disulfide bond with C at the base of ECL3.

Figure 10:
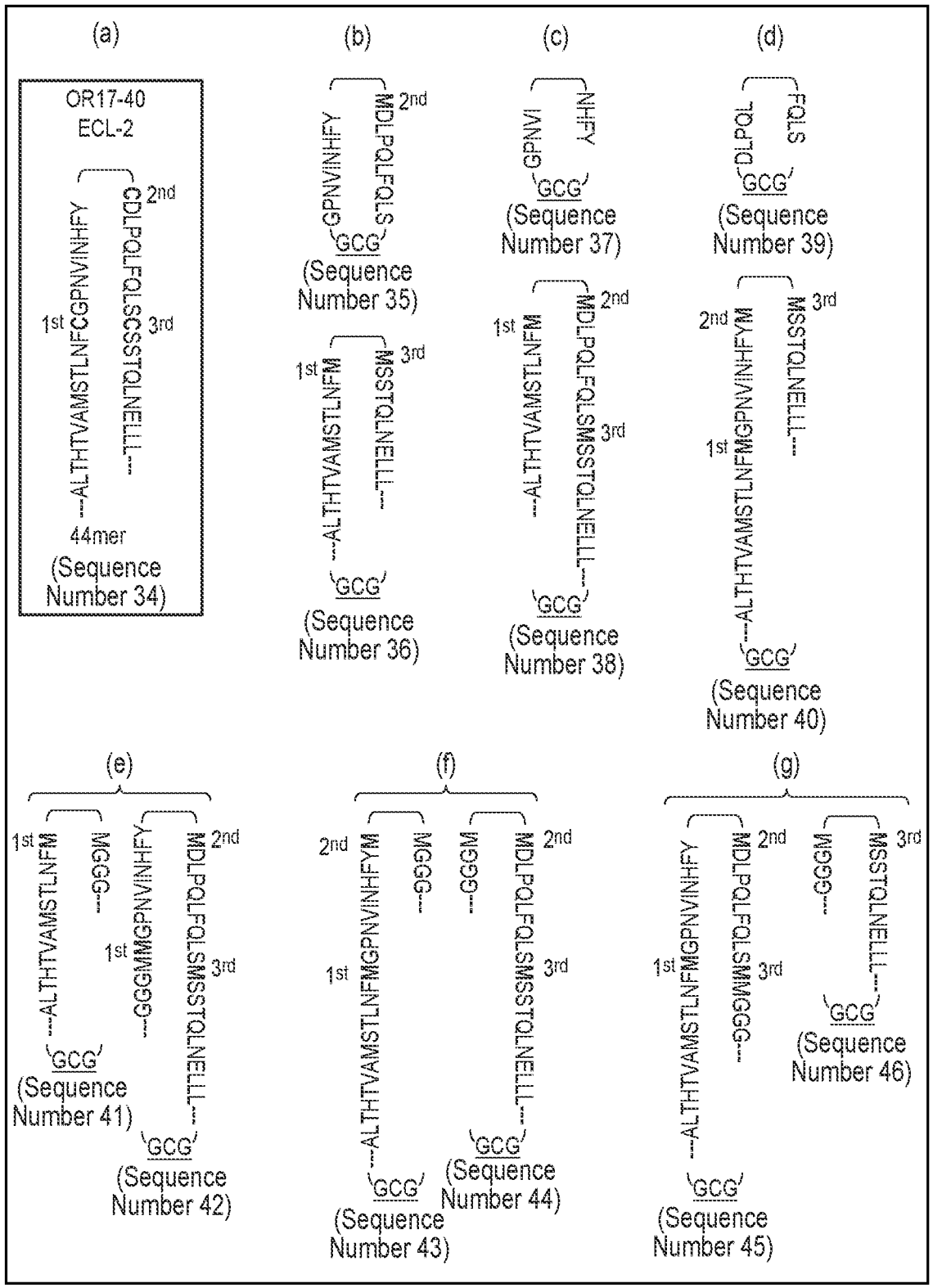
FIG. 10 is a diagram illustrating an example of an amino acid sequence of the extracellular region used for the first ECR peptide or a second ECR peptide of the embodiment.

In addition, the following amino acid sequence of ECL-2 of OR 17-40 illustrated in (a) of FIG. 10 has a length of 44 mer. ALTHTVAMSTLNFCGPN-VINHFYCDLPQLFQLSCSSTQLNELLL (SEQ ID NO: 34)

Since synthesis may be difficult if all of this amino acid sequence is used, it may be divided into a plurality of rings. For example, when a plurality of Cs is contained in the amino acid sequence, there is a high possibility that the C and C are originally bonded to each other to form a ring. Therefore, in order to bring the shape as close as possible to such an original shape, it is preferable that the length is less than 40 mer by division with the position of C as a reference.

For example, when three Cs included in the ECL-2 are $1^{st}$-C, $2^{nd}$C, and $3^{rd}$C from the N-terminal side, the sequence between any two Cs can be divided as illustrated in parts (b) to (g) of FIG. 10. In the example of FIG. 10, since C (GCG) is inserted and bound, C in the middle of the sequence is substituted with M. For example, as illustrated in part (b) of FIG. 10, the sequence between $1^{st}$C and $3^{rd}$C can be divided (SEQ ID NOs: 35 and 36). Alternatively, as illustrated in parts (c) and (d) of FIG. 10, a pattern of dividing the sequence between $1^{st}C$ and $2^{nd}C$ (SEQ ID NOs: 37 and 38) or the sequence between $2^{nd}C$ and $3^{rd}C$ (SEQ ID NOs: 39 and 40) is also possible.

Alternatively, on the assumption that C of ECL-2 bonded to C at the base of ECL-1, the sequence may be divided into a sequence from $1^{st}C$ to the N-terminal side and a sequence from $1^{st}C$ to the C-terminal side as illustrated in part (e) of FIG. 10 (SEQ ID NOs: 41 and 42). In addition, MGGG may be added to the C-terminal side of $1^{st}C$ to the ring having the N-terminal side from $1^{st}C$, and MGGG may be added to the N-terminal side of $1^{st}C$ to the ring having the C-terminal side from $1^{st}C$. Similarly, as illustrated in parts (f) and (g) of FIG. 10, a pattern in which the sequence is divided into sequences on the N-terminal side and the C-terminal side with $2^{nd}C$ or $3^{rd}C$ as a reference is also possible ((f): SEQ ID NOs: 43 and 44, (g): SEQ ID NOs: 45 and 46). Both divided rings may be used, or only one ring may be used.

In a further embodiment, as illustrated in FIG. 11A, the first ECR 4 may contain sequences derived from a plurality of extracellular regions, or as illustrated in FIG. 12A, the second ECR peptide 6 may contain sequences derived from a plurality of extracellular regions.

For example, as illustrated in FIG. 11A, when two extracellular regions are used for the first ECR 4, the two extracellular regions are immobilized to the sensitive film 3. It is also possible to bond the above-described immobilizing peptide to each and immobilize the peptide to the sensitive film, but one extracellular region may be bonded to each end of the following sequence:

GGG-RGAGAGAR-GGG (SEQ ID NO: 47). In the case of using ECL, it may be bonded via a binder such as maleimide in the same manner as described above. When the extracellular terminal is used, an amino acid sequence connected to SEQ ID NO: 47 may be synthesized. For example, when a transmembrane receptor including three ECLs and one extracellular C-terminal as illustrated in FIG. 3 is used, 6 combinations are conceivable as illustrated in FIG. 11C.

As illustrated in FIG. 12A, for example, two kinds of extracellular regions can be used for the second ECR 6. In that case, two extracellular regions are added into the liquid phase 5. Each of them may be added individually, or two kinds thereof may be added in a connected manner as illustrated in FIG. 12B. In that case, if necessary, it can be bonded via a binder such as maleimide and/or GGG. For example, when a transmembrane receptor including three ECLs and one extracellular C-terminal as illustrated in FIG. 3 is used, 6 combinations are conceivable as illustrated in FIG. 12C.

Which extracellular region is used for the first ECR4 or the second ECR6 may be determined from past knowledge such as literature, for example. For example, it is preferable to use a portion known to be bonded to the target substance 10. Alternatively, the determination may be made by verifying a combination in which the detection sensitivity of the target substance 10 is excellent by an experiment. Alternatively, it is also preferable to use a water-soluble one as the second ECR6 and a hydrophobic one as the first ECR4 depending on the type and shape of the amino acid to be contained.

Hereinafter, another configuration of the chemical sensor 1 will be described.

(Substrate)

A substrate 2 has, for example, a rectangular plate shape. The substrate 2 is, for example, silicon, glass, ceramics, a polymer material, or the like. For example, the substrate 2 may include an insulating film on the surface on the sensitive film 3 side. The insulating film is, for example, silicon oxide, silicon nitride, aluminum oxide, a polymer material, or the like.

(Sensitive Film)

The sensitive film 3 is formed of a substance whose physical properties, for example, electric resistance, change when the structure of the substance bonded to the sensitive film 3, the state of charge, and the like change. The sensitive film 3 is preferably graphene, but may be formed of another two-dimensional material such as molybdenum disulfide ($MoS_2$) or tungsten diselenide ($WSe_2$). Alternatively, a carbon nanotube, an ISFET, or the like may be used instead of the sensitive film.

When the sensitive film 3 is graphene, it may be a single-layer graphene film or a multi-layer graphene film having a thickness of one carbon atom. The size of sensitive film 3 is not limited, but can be, for example, about 5 to 100 μm in width and about 5 to 100 μm in length. Alternatively, for example, a nanoribbon shape having about 100 to 500 nm in width and about 200 nm in length can be used.

In addition, the surface of the sensitive film 3 is preferably blocked so that impurities or the target substance 10 is not directly bonded to the sensitive film 3. For example, blocking can be performed by coating the surface of the sensitive film 3 with a blocking reagent such as a metal oxide ($Al_2O_3$, $HfO_2$, and the like), a protein, an organic molecule, a lipid membrane, or a peptide. As the blocking reagent, an appropriate blocking reagent may be used depending on the type of specimen or the like, but for example, the blocking reagent may be the same substance as the target substance 10. For example, when the target substance 10 is limonene, it is also possible to block non-specific adsorption of limonene to the sensitive film 3 with limonene.

The blocking can be performed, for example, as follows. First, a buffer solution, for example, 1 mM HEPES is dropped onto the sensitive film 3, and monitoring of a change in the physical properties of the sensitive film 3 is started. In the configuration of the FET, the gate voltage and the drain voltage are applied to start the measurement of the drain current. Next, the buffer solution is substituted with a solution containing a blocking reagent to add the blocking reagent onto the sensitive film 3, and the sensitive film 3 is left for about 1 minute. When the blocking reagent adheres to the sensitive film 3, the physical properties of the sensitive film 3 change. Therefore, the blocking is completed by repeatedly performing substitution with a solution containing the blocking reagent until the change in the physical properties disappears.

(Liquid Phase)

The liquid phase 5 is a liquid disposed on the sensitive film 3, and is, for example, water, physiological water, an ionic liquid, a buffer solution, or the like. An organic solvent may be contained as long as the bonding ability of the peptide is not impaired. The thickness of the liquid phase 5 is not particularly limited, and is, for example, about several mm.

(Electrode)

The material of the first electrode 7 and the second electrode 3 is, for example, metal such as gold (Au), silver (Ag), copper (Cu), palladium (Pd), platinum (Pt), nickel (Mi), titanium (Ti), chromium (Cr), or aluminum (Al), or a conductive substance such as zinc oxide (ZnO), indium tin oxide (ITO), IGZO, or a conductive polymer.

(Insulator)

An insulator 9 can be formed of, for example, a polymer substance such as an acrylic resin, polyimide, polybenzoxazole, an epoxy resin, a phenol resin, polydimethylsiloxane, or a fluororesin, or an inorganic insulating film such as silicon oxide, silicon nitride, or aluminum oxide.

The substrate 2, the first electrode 7, the second electrode 8, and the insulator can be manufactured by a semiconductor process.

The mechanism for detecting the change in the physical properties of the sensitive film 3 of the chemical sensor 1 is not limited to the configuration of FIG. 1, and for example, another charge detection element such as a surface plasmon resonance element (SPR), a surface acoustic wave (SAW) element, a piezoelectric thin film resonance (FBAR) element, a quartz crystal microbalance (QCM) element, or a MEMS cantilever element can be used.

In a further embodiment, there is provided a chemical sensor including a plurality of sensor elements in which a configuration for detecting one sensitive film 3 and a change in the physical properties thereof are set as one unit, that is, one sensor element. The first ECR peptide 4 and the second ECR peptide 6 derived from different types of transmembrane receptors are used among a plurality of sensor elements, and different types of target substances 10 can be detected.

Figures 13A, 13B:
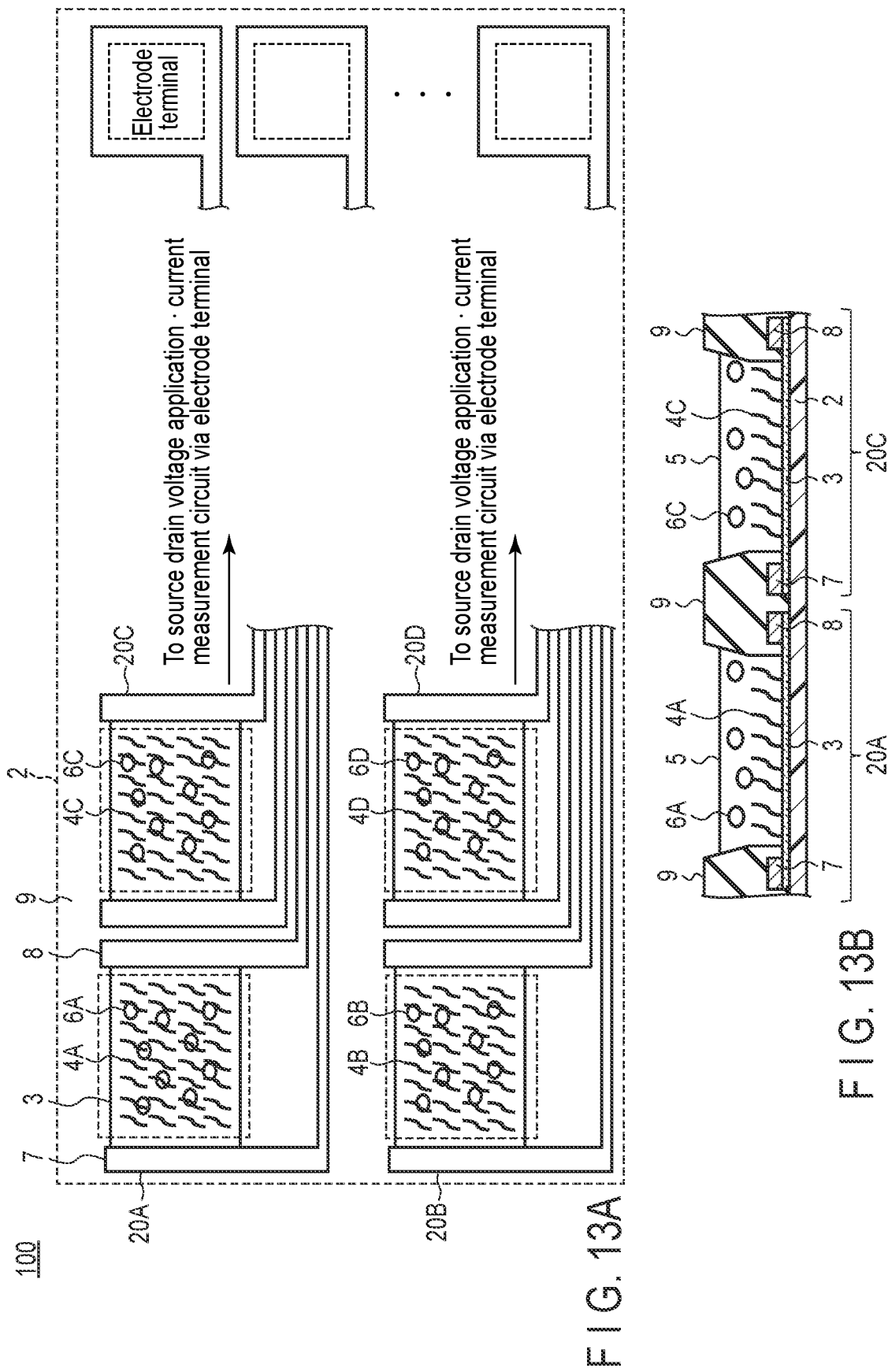
FIG. 13A is a plan view illustrating an example of a chemical sensor including a plurality of sensor elements according to the embodiment.
FIG. 13B is a cross-sectional view thereof.

As illustrated in FIGS. 13A and 13B, a chemical sensor 100 including a plurality of sensor elements includes a sensor element 20A including a first ECR peptide 4A and a second ECR peptide 6A derived from a transmembrane receptor A, a sensor element 20B including a first ECR peptide 4B and a second ECR peptide 6B derived from a transmembrane receptor B, a sensor element 20C including a first ECR peptide 4C and a second ECR peptide 6C derived from a transmembrane receptor C, and a sensor element 20D including a first ECR peptide 4D and a second ECR peptide 6D derived from a transmembrane receptor D. Each of the sensor elements 20A to 20D is configured to individually detect a change in the physical properties of the sensitive film 3. The source electrode and the drain electrode of each sensor element are connected to wiring, and the wiring is connected to an electrode terminal. For example, a bonding wire is connected to the electrode terminal, and the bonding wire is connected to a voltage-current circuit.

The liquid phase 5 of each sensor element 20 is isolated from the adjacent sensor element 20. Isolation of the liquid phase 5 prevents the second ECR peptide 6 from mixing with ether sensor elements 20. Alternatively, the second ECR peptide 6 for a plurality of sensor elements 20 may be mixed and used. In this case, it is not necessary to isolate the liquid phase 5.

The number, type, arrangement, and the like of the sensor elements 20 mounted on one chemical sensor 100 are not limited to those illustrated in FIG. 3. For example, by mounting about 10 sensor elements 20 on one chemical sensor and immobilizing the first ECR peptide 4 on about half of the sensor elements, the presence or absence of the target substance can be accurately determined from the difference between the signals of the sensor element on which the first ECR peptide 4 is immobilized and the sensor element on which the first ECR peptide 4 is not immobilized. Alternatively, a plurality of sensor elements 20 of a specific type may be provided.

According to such a chemical sensor 100, a plurality of types of target substances 10 can be detected from one type of specimen. For example, it is also possible to use a plurality of target substances 10 included in a specific odor as detection targets.

Method for Detecting Target Substance

Hereinafter, a method for detecting a target substance 10 using the chemical sensor 1 of the embodiment will be described. The detecting method is a method for detecting the target substance 10 in the specimen.

The specimen is, for example, a gas, such as air, exhalation, or a gas generated from an analysis target such as a living body or an object, or air around the analysis target. The target substance 10 in the gas specimen is, for example, a volatile organic compound (VOC) such as alcohols, esters, or aldehydes, and may be, for example, an odor substance, a pheromone substance, or the like. The target substance 10 is, for example, a hydrophobic substance.

The specimen may be a liquid, and may be, for example, a liquid derived from a living body such as blood, serum, plasma, blood cells, urine, feces, sweat, saliva, sputum, lymph, spinal fluid, lacrimal fluid, breast milk, amniotic fluid, semen, a cell extract, a tissue extract, or a mixture thereof. Alternatively, the specimen may be a specimen derived from an environment such as soil, river water, sea water, or a mixture thereof. Alternatively, the liquid may be a liquid derived from a food product, a cosmetic product, an industrial product, or the like.

Figure 14:
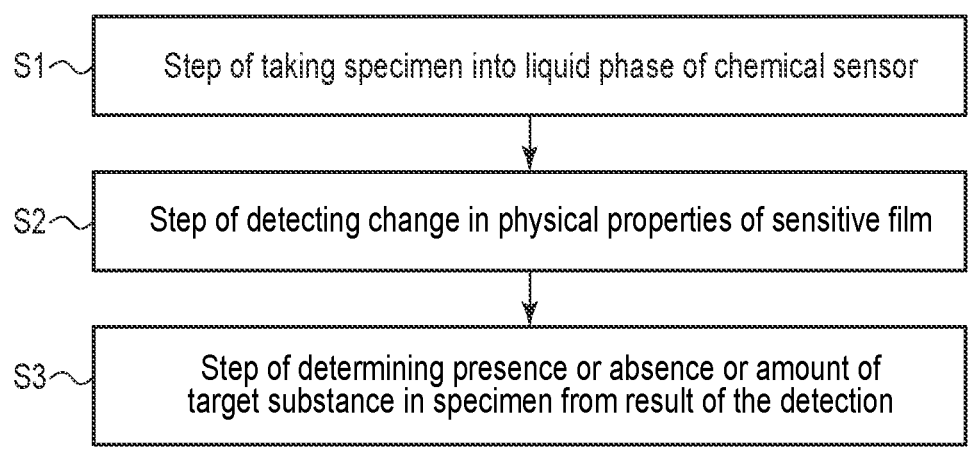
FIG. 14 is a flowchart illustrating an example of a detecting method according to the embodiment.

The method for detecting the target substance 10 of the embodiment includes the following steps, for example, as illustrated in FIG. 14.

The method for detecting the target substance 10 includes, for example, the following steps: taking a specimen into a liquid phase of a chemical sensor (specimen taking step S1), detecting a change in physical properties of a sensitive film (detecting step S2), and determining presence or absence or an amount of the target, substance 10 in the specimen from a result of the detection (determination step S3).

Hereinafter, specific examples of the procedure of each of the above steps will be described.

(Specimen taking Step S1)

For example, when the specimen is a gas, the specimen is brought into contact with the liquid phase 5 of the chemical sensor 1 to be taken into the liquid phase 5. The contact can be performed using, for example, a specimen intake device 200 using bubbling as illustrated in FIG. 15. The specimen intake device 200 includes a buffer solution supply tank 201 that stores a buffer solution and a vapour-liquid phase intake portion 202. The buffer solution supply tank 201 and the vapour-liquid phase intake portion 202 are connected to each other by a channel 203, and a new buffer solution is supplied from the buffer solution supply tank 201 to the vapour-liquid phase intake portion 202. The channel 203 may include a pump 204 and a valve 205. The vapour-liquid phase intake portion 202 includes a container, a channel 207 including an atmosphere collection port 206 for sending a specimen (for example, odor atmosphere) to a buffer solution in the container, and a channel 206 for discharging a gas in the container. In the container, the specimen atmosphere supplied from the channel 207 is bubbled in the buffer solution, and the target substance 10 is taken into the buffer solution. This buffer solution is sent to the chemical sensor 1 via a channel 209 attached to the container. The channel 209 may include, for example, a valve 210 and a pump 211. In addition, the vapour-liquid phase intake portion 202 includes a drainage channel 212 attached to the container, and drains excess liquid therefrom. The drainage channel 212 may include a valve 213.

Figure 17:
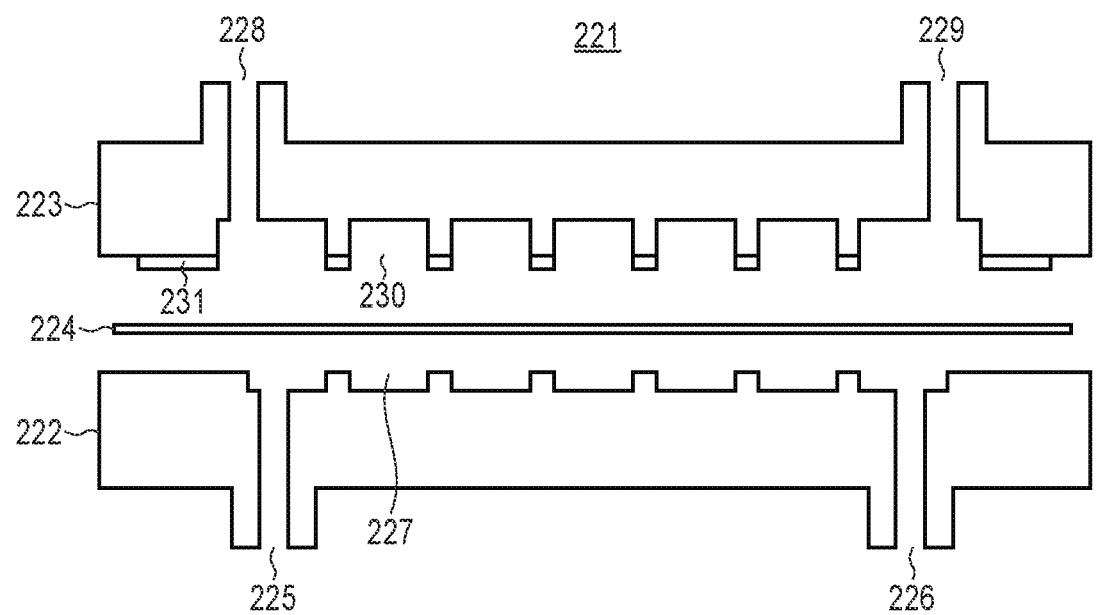
FIG. 17 is a cross-sectional view illustrating an example of a vapour-liquid phase intake portion including a porous membrane of the embodiment.

Alternatively, the specimen intake device 220 illustrated in FIG. 16 may be used. The specimen intake device 220 includes a vapour-liquid phase intake portion 221 including a porous membrane instead of the vapour-liquid phase intake portion 202 that performs the bubbling. As illustrated in FIG. 17, the vapour-liquid phase intake portion 221 includes a channel chip 222, a lid 223 of the channel chip, and a porous membrane 224 sandwiched therebetween. The channel chip 222 is formed with a solvent inlet 225 connected to the channel 203 from the buffer solution supply tank 201, a solution outlet 226 connected to the channel 209 following the chemical sensor, and a channel 227 connecting the solvent inlet 225 to the solution outlet 226. The lid 223 includes a specimen atmosphere inlet 228 connected to a channel 207 for taking a specimen, a gas discharge port 229 connected to a channel 203 for discharging gas, a groove 230 having a depth of about 1 to 2 mm dug in a shape corresponding to the channel 221, and an elastic body 231 (for example, rubber) attached to a portion in contact with the channel chip 222. As the porous membrane 224, for example, a porous polymer material such as PTFE or polyamide can be used.

In the specimen intake device 220, the buffer solution is caused to flow into the channel 227 from the solvent inlet 225, and the specimen atmosphere is taken in from the specimen atmosphere inlet 223, and thereby the target substance 10 is taken into the buffer solution through the porous membrane 224 in the channel 227. This buffer solution is sent to the chemical sensor 1 via a channel 209 attached to the solution outlet 226.

Figure 18:
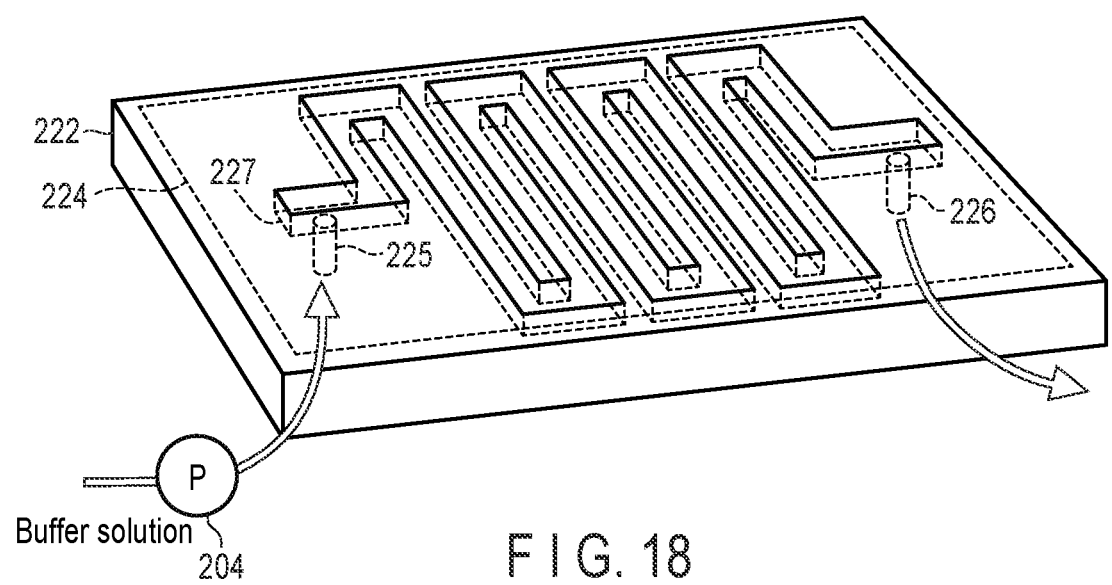
FIG. 18 is a perspective view illustrating an example of a channel of the vapour-liquid phase intake portion including the porous membrane of the embodiment.

The channel 227 is preferably a flat and meandering channel as illustrated in FIG. 18 in order to increase the contact time between the specimen atmosphere and the buffer solution and increase the specific surface area for non-contact.

Figure 19:
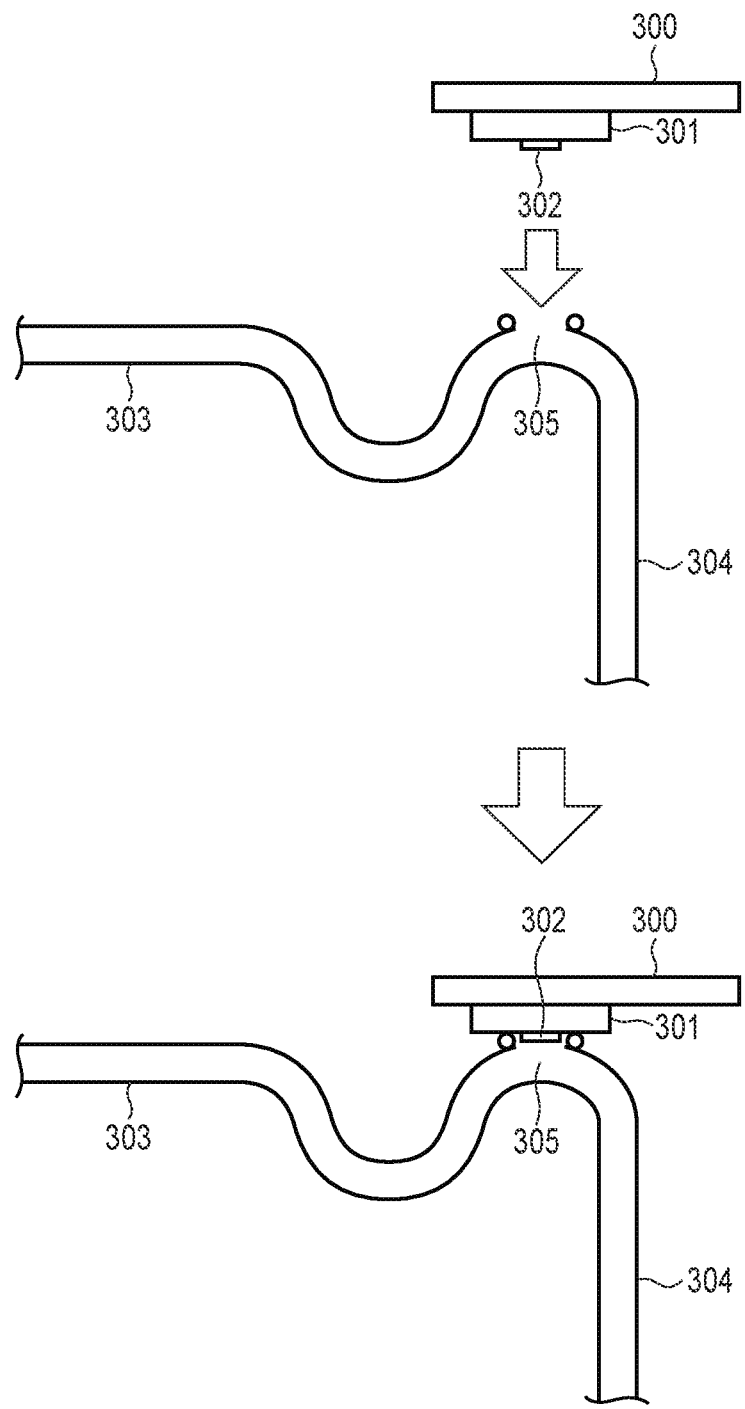
FIG. 19 is a diagram illustrating an example of a cartridge substrate attaching method according to an embodiment.

Note that the chemical sensor 1 may be a consumable part, and in that case, it is preferable that the chemical sensor 1 is detachable from the entire sensor device including, for example, the specimen intake device. For example, as illustrated in FIG. 19, the sensor chip 301 on which the chemical sensor 302 is formed is mounted on the cartridge substrate 300. Further, a sensor exposure window 305 is provided in a pipe 303 (for example, the channel 209 in FIGS. 15 and 16) through which the liquid phase 5 and the liquid phase 5 taking in the specimen flow. The sensor exposure window 305 is an opening, and the sensor cartridge can be attached and detached such that the chemical sensor 1 is exposed to the opening. The pipe 306 downstream of the sensor exposure window 305 is connected to a liquid discharge port (not shown) for discharging liquid.

When the specimen is a liquid, the specimen is taken into the liquid phase 5 by being dropped onto the liquid phase 5. In the present method, the chemical sensor 1 includes a first ECR peptide 4 and a second ECR peptide 6 derived from a transmembrane receptor that is bonded to the target substance 10. Therefore, as described in FIG. 2, the target substance 10 is bonded to the second ECR peptide 6 present in the liquid phase 5, and further bonded to the first ECR peptide 4 immobilized on the sensitive film 3. As a result, the target substance 10 is bonded to the sensitive film 3 in a state of being sandwiched between the first ECR peptide 4 and the second ECR peptide 6. This bonding changes the physical properties of the sensitive film 3. The physical properties are, for example, electric resistance of the sensitive film 3.

On the other hand, since the first ECR peptide 4 and the second ECR peptide 6 specifically are bonded to the target substance 10, substances (impurities) that are not targets are not bonded to the sensitive film 3. Therefore, impurities are prevented from affecting changes in the physical properties of the sensitive film 3.

(Detecting Step S2)

Next, a change in the physical properties of the sensitive film 3 is detected. For example, the detection is performed by a mechanism that converts a change in the physical properties of the sensitive film 3 into a change in an electrical signal. The electrical signal is, for example, a current value, a potential value, an electric capacitance value, an impedance value, or the like. The change in the electrical signal is, for example, an increase, a decrease, or a disappearance of the electrical signal, a change in an integrated value within a specific time, or the like. When the configuration of the FET illustrated in FIG. 1 is used, a change in the physical properties can be detected as a change in a drain current value or the like.

(Determination Step S3)

Next, the presence or absence or the amount of the target substance 10 in the specimen is determined from the detection result. For example, it can be determined that the target substance 10 is present in the specimen in a case where there is a change in the electrical signal, a case where a change amount or a change rate of the signal is larger than a threshold value, or the like. The threshold can be obtained, for example, by subjecting a specimen known to contain the target substance 10 to analysis of a chemical sensor to obtain a change value of an electrical signal. In addition, the amount of the target substance 10 may be determined by preparing a calibration curve of a change amount or a change rate with respect to the concentration of the target substance 10 using the target substance 10 whose concentration is known and comparing with the calibration curve. On the other hand, it may be determined that the target substance 10 is not present in a case where no change occurs or a case where the change amount or the change rate of the signal is smaller than the threshold value.

Through the steps described above, the target substance 10 in the specimen can be specifically and highly sensitively detected.

According to the present method, by using the plurality of extracellular regions of the transmembrane receptor as the first ECR peptide 4 and the second ECR peptide 6, and by circularizing and using the ECL, the original three-dimensional structure of the transmembrane receptor that surrounds and captures the ligand by the plurality of extracellular regions can be reproduced, and the strong affinity, selectivity, and specificity inherent in the receptor can be realized.

In addition, for example, since the target substance 10 has a low molecular weight, even if the target substance 10 is directly bonded to the sensitive film 3, the influence on the change in the physical properties of the sensitive film 3 may be slight. According to the present method, by bonding the first ECR peptide 4 and the second ECR peptide 6 to the sensitive film 3, the molecular weight of the substance bonded to the sensitive film 3 as a whole increases, so that the change in the physical properties of the sensitive film 3 is further increased, and detection can be performed with higher sensitivity.

Furthermore, by inserting, for example, cysteine into the joint of the circularized ECLs, the extracellular sequence is dimerized in a shape facing outward, so that the capturing ability for the target substance 10 is improved, and the detection sensitivity can be further improved.

When the chemical sensor 100 including the plurality of types of sensor elements 20 is used, the specimen taking step S1 to the determination step S3 may be performed in the same manner. However, in the detecting step S2, a change in the physical properties of the sensitive films 3 is individually detected from each sensor element 20. In the determination step S3, the presence or absence or the amount of the corresponding target, substance 10 is determined for each sensor element 20 from the individually obtained detection result. Thereafter, the composition ratio of the plurality of target, substances 10 contained in the specimen can be determined from the type (that is, the type of transmembrane receptor from which the first ECR peptide 4 and the second ECR peptide 6 immobilized thereon are derived), number, and/or ratio of the sensor element 20 in which the target substance 10 is determined to be present.

For example, the type of the target substance 10 group may be specified from the composition ratio. For example, the specific odor may include a plurality of types of the target substances 10 at a specific composition ratio. Therefore, by combining a certain odor as the target substance 10 group having a specific composition ratio, the presence or absence or the amount of the odor may be determined by the above method. In addition, it is also possible to associate an odor with a cause of emitting the odor (for example, foods and beverages, narcotics, subjects having diseases, and the like) in advance and specify the cause of emitting the odor by such detection. The target associated with the type of the target substance 10 group is not limited to the odor, and may be, for example, a state of a specimen or a health state of a living body that provides the specimen.

In one embodiment, step from S1 to S3 may be continuously carried out without performing another step between any of these steps.

Apparatus for Detecting Target Substance

The detecting method may be performed by a detecting apparatus that automatically performs each step. As illustrated in FIG. 20, the detecting apparatus 500 includes, for example, a detection unit 510 that includes the chemical sensor 1 and converts a change in the physical properties of the sensitive film 3 into a change in an electrical signal, a specimen introduction unit 520 that takes a specimen into the liquid phase 5 of the chemical sensor 1, and a processor 530 that determines the presence or absence or the amount of the target substance 10 by processing information of the electrical signal obtained from the detection unit 510.

For example, in a case of assuming a specimen of gas, the specimen introduction unit 520 includes a specimen intake port 521 (atmosphere collection port 206) for taking the specimen from the outside, a liquid phase tank (buffer solution supply tank) 201, vapour-liquid phase intake portions 202 and 221, and an exhaust port 523 (blower 522 that sends exhaust air to exhaust hole 523, if necessary) for exhausting the specimen gas at that time. These may be the specimen intake device 200 or 220 illustrated in FIGS. 15 and 16. In the case of assuming the liquid specimen, although not illustrated, for example, a liquid-tight container that accommodates the specimen, a channel that sends the specimen from the container onto the liquid phase 5 of the chemical sensor 1, a pipette, or the like is provided.

The detection unit 510 includes, for example, the chemical sensor 1, a voltage application circuit 511 that applies a voltage to the chemical sensor 1, and a current measurement circuit 512 for measuring a change in the physical properties of the sensitive film 3 as an electrical signal. Furthermore, the detection unit may include a pump 513 that sends the liquid phase to a liquid discharge port 514 that discharges the liquid phase 5 after detection or the excess liquid phase 5.

The processor 530 includes, for example, a storage device 531 and a processing device 532. The storage device 531 is, for example, a memory, and stores a measurement value from an ammeter 512, a threshold of the measurement value, a calibration curve, a calculation formula and a determination result used for determining the presence or absence or the amount of the target substance 10 from the measurement value, a program for performing determination, a program for automatically performing the operation of each unit, and the like. The processing device 532 is, for example, a CPU or the like, and determines the presence or absence or the amount of the target substance 10 based on a program and sends a command to each unit.

The respective units are electrically connected to each other by, for example, a bus 540.

The detecting apparatus 500 may further include an input unit that inputs a parameter, a display unit that outputs a determination result, and the like.

Examples

Hereinafter, an example in which the chemical sensor of the embodiment is manufactured and used will be described.

A graphene FET sensor element including two types of graphene films was manufactured:

(1) Two graphene films on which the first ECR peptide 4 is immobilized and limonene is adsorbed, and (2) Two graphene films on which the first ECR peptide 4 is not immobilized and limonene is adsorbed.

The adsorption of limonene was performed as follows. First, 1 mM of HEPES was dropped onto a graphene film, and a drain current was started to be measured at a gate voltage of 300 mV. Next, while measuring the drain current, the solution (1 mM of HEPES aqueous solution +1% DMSO) was substituted with 10 μM of a limonene solution and left for 1 minute. This was repeated until there was no change in the drain current at the time of substitution.

The first ECR peptide 4 of (1) was immobilized as follows. The liquid on the graphene film was substituted with pure water, and then substituted with 500 nM of solution (aqueous solution) of [3-maleimidopropanoyl]-GGG-RGAGAGAR. Thereafter, a self-assembled film of [3-maleimidopropanoyl]-GGG-RGAGAGAR was formed on the graphene film by leaving it for 1 hour. Next, the liquid on the graphene film was substituted with pure water, and then ECL-1 (SEQ ID NO: 8) of OR19a was substituted with 500 nM of solution (0.5% aqueous DMSO, with 50 μM of TCEP) of the cyclized peptide. After 10 minutes, the gate voltage application and the drain current measurement, were completed. This was left to stand for overnight to allow maleimide and thiol to be bonded to each other.

Next, one of the graphene FST sensor elements (Example 1) in the above (1) was subjected to the following processing. In order to remove the excess first ECR peptide 4, the liquid on the sensitive film 3 was substituted with 1 mM of HEPES, and then further substituted with 1 μM of solution (1 mM of HEPES, with 2% DMSO) of the second ECR peptide 6 to form a liquid phase. As the second ECR peptide 6, a peptide obtained by circularizing EC1-2 (SEQ ID NO: 11) of OR19a was used. The drain current v/as measured while scanning the gate voltage between 0 to 700 mV to measure a charge neutral point. Next, the gate voltage was set to a value 200 mV lower than the charge neutral point voltage, and the drain current measurement was started.

Subsequently, the liquid phase was sequentially substituted with 1 μM of solution (1 mM of HEPES, with 2% DMSO) of the second ECR peptide 6 containing limonene at concentrations of 10 nM, 100 nM, 1 μM, and 10 uM, respectively, and the change in the drain current value was measured. Incidentally, before the solution containing limonene at each concentration was added, the liquid phase was once substituted with a solution containing no limonene to refresh the liquid phase. In addition, limonene was similarly detected using a solution containing the second ECR peptide 6 in one of the graphene films of (2) (Comparative Example 1). In the other of the graphene films of the above (1), limonene was similarly detected using a limonene-containing solution not containing a solution containing no second ECR peptide 6 (Comparative Example 2). In addition, also in one of the graphene films of the above (5), limonene was similarly detected using a limonene-containing solution not containing a solution containing no second ECR peptide 6 (Comparative Example 3). In Comparative Examples 1 to 3, the experiment was also performed at a limonene concentration of 10 nM.

FIG. 21 illustrates a change in the drain current value with respect to time(s) in Example 1. A change (decrease) in the drain current value was observed when the solution containing limonene was added. In addition, it was confirmed that the current value returned to the original value when the solution containing no limonene was added.

On the other hand, a change in the drain current value with respect to the time(s) in Comparative Example 3 is illustrated in FIG. 22. The drain current value decreased with time regardless of the presence or absence of limonene. Therefore, it was not possible to detect the limonene. Although the drain current value slightly decreased when 10 nM of limonene was added, the drain current value returned to the baseline before the next, substitution, and thus this is estimated to be noise of pipetting.

Figure 23:
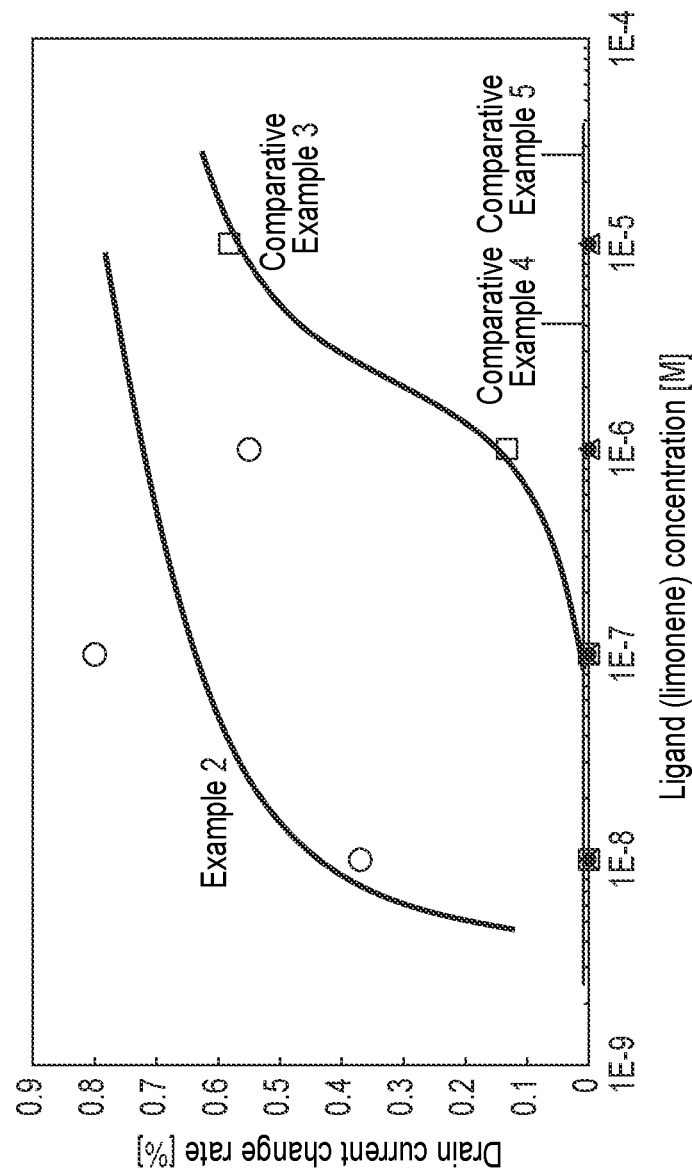
FIG. 23 is a graph illustrating experimental results of Example 1 and Comparative Examples 1 to 3.

The detected change rate (%) of the drain current with respect to the concentration (M) of limonene in each example is illustrated in FIG. 23 and Table 2.

TABLE 2

| Limonene concentration (M) | Example 1 ECL1 × ECL2 | Comparative Example 1 ECL1 × NA | Comparative Example 2 NA × ECL2 | Comparative Example 3 NA × NA |
|---|---|---|---|---|
| 1E-8 | 0.37 | 0.00 | 0.00 | 0.00 |
| 1E-7 | 0.80 | 0.00 | 0.00 | 0.00 |

TABLE 2-continued

| Limonene concentration (M) | Example 1 ECL1 × ECL2 | Comparative Example 1 ECL1 × NA | Comparative Example 2 NA × ECL2 | Comparative Example 3 NA × NA |
|---|---|---|---|---|
| 1E-6 | 0.55 | 0.13 | 0.00 | 0.00 |
| 1E-5 | — | 0.58 | 0.00 | 0.00 |

In Example 2, the drain current value was the highest at any concentration of limonene, and it was clear that it is possible to detect limonene with the highest sensitivity. In particular, it was possible to detect limonene of IE-8 (10 nM) and IE-7 (100 nM) only in Example 1. The reason why the drain current change rate of 1E-6 was not larger than that of IE-7 is presumed to be that the concentration of limonene was the same as that of the second ECR peptide 6, so that limonene was bonded to both the first ECR peptide and the second ECR peptide, and thereby the formation of a sandwich bond was inhibited. In Comparative Example 1, a change in the current value according to the concentration was observed at a concentration higher than that of IE-6, but the sensitivity was lower than that in Example 1. In Comparative Example 2 and Comparative Example 3, the current change rate was 0% at any concentration.

Therefore, it was suggested that the target substance can be detected with high sensitivity by using both the first ECR peptide 4 and the second ECR peptide 6.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A chemical sensor for detecting a target substance in a specimen, the chemical sensor comprising:
   a sensitive film;
   a first extracellular region peptide of a transmembrane receptor immobilized on the sensitive film;
   a liquid phase disposed on the sensitive film; and
   a second extracellular region peptide of the transmembrane receptor contained within the liquid phase,
   wherein the extracellular region is an extracellular loop, and
   the first extracellular region peptide and the second extracellular region peptide contain at least a part of amino acid sequence of the extracellular loop, and are circularized.

2. The chemical sensor according to claim 1, further comprising: a first electrode connected to one end of the sensitive film; and a second electrode connected to the other end of the sensitive film, wherein the sensitive film is made of graphene.

3. The chemical sensor according to claim 1,
   wherein the transmembrane receptor includes a plurality of extracellular regions, and
   the first extracellular region peptide and the second extracellular region peptide each contain at least a part of amino acid sequence of the mutually different extracellular regions of the transmembrane receptor.

4. The chemical sensor according to claim 3, wherein the part of the amino acid sequence is less than 40 mer.

5. The chemical sensor according to claim 1, further comprising: a plurality of the sensitive films, wherein the liquid phase is isolated for each of the plurality of sensitive films, and the first extracellular region peptides and the second extracellular region peptides are derived from transmembrane receptors different from each other among the plurality of sensitive films.

6. A detecting apparatus comprising: the chemical sensor according to claim 1; a detection unit that converts a change in physical properties of the sensitive film into a change in an electrical signal; a specimen introduction unit that takes the specimen into the liquid phase of the chemical sensor; and a processor that determines presence or absence or an amount of a target substance in the specimen by processing information of the electrical signal obtained from the detection unit.

* * * * *